(12) United States Patent
Murthy et al.

(10) Patent No.: US 7,815,946 B1
(45) Date of Patent: Oct. 19, 2010

(54) ANTI-DIABETIC AND CHOLESTEROL LOWERING PREPARATION FROM FENUGREEK SEEDS

(75) Inventors: Pothapragada Suryanarayana Murthy, Noida (IN); Radha Moorthy, New York, NY (US); K. M. Prabhu, Delhi (IN); Dinesh Puri, Delhi (IN)

(73) Assignee: Diakron Pharmaceuticals, Inc., Morris Plains, NJ (US)

( * ) Notice: Subject to any disclaimer, the term of this patent is extended or adjusted under 35 U.S.C. 154(b) by 2 days.

(21) Appl. No.: 11/182,494

(22) Filed: Jul. 15, 2005

Related U.S. Application Data

(63) Continuation of application No. 10/117,444, filed on Apr. 4, 2002, now abandoned.

(60) Provisional application No. 60/282,372, filed on Apr. 5, 2001.

(51) Int. Cl.
*A61K 35/78* (2006.01)

(52) U.S. Cl. .................................................. 424/757

(58) Field of Classification Search ................ None
See application file for complete search history.

(56) References Cited

U.S. PATENT DOCUMENTS

| | | | |
|---|---|---|---|
| 5,277,910 A * | 1/1994 | Hidvegi | 424/757 |
| 5,847,109 A * | 12/1998 | Garti et al. | 536/123 |
| 5,997,877 A * | 12/1999 | Chang | 424/757 |
| 6,063,402 A * | 5/2000 | Gebert et al. | 424/464 |
| 6,080,401 A * | 6/2000 | Reddy et al. | 424/93.3 |
| 6,495,175 B2 * | 12/2002 | Rao et al. | 424/757 |
| 7,141,254 B2 * | 11/2006 | Bhaskaran et al. | 424/754 |
| 7,338,675 B2 * | 3/2008 | Lee et al. | 424/757 |
| 7,338,941 B2 | 3/2008 | Bibbs et al. | 514/27 |
| 2001/0024665 A1 * | 9/2001 | Rao et al. | 424/757 |
| 2003/0077339 A1 * | 4/2003 | Yoon et al. | 424/725 |
| 2004/0156920 A1 * | 8/2004 | Kane | 424/725 |

OTHER PUBLICATIONS

Alcock et al "Stereochemistry of the 4-Hydroxyisoleuciine from *Trigonella foenum-graecum*" 1989 Phytochemistry vol. 28, No. 7 pp. 1835-1841.*

Bordia et al "Effect of ginger (*Zingiber officinale* Rosc.) and fenugreek (*Frigonella foenumgraecum* L.) on blood lipids, blood sugar and platelet aggregation in patients with coronary artery disease" 1997 Prostaglandins Leukotrienos and Essential Fatty Acids 56 (5) pp. 379-384.*

* cited by examiner

*Primary Examiner*—Herbert J. Lilling
(74) *Attorney, Agent, or Firm*—Pillsbury Winthrop Shaw Pittman LLP

(57) ABSTRACT

The invention relates to a composition having blood glucose-lowering and cholesterol-lowering activity that can be obtained from seeds of the Papilinaceae Leguminosae family, for example, fenugreek seed. Methods of obtaining the composition from seed and seed parts are provided. Therapeutic methods of using the composition, such as for treating diabetes and hypercholesterolemia, are also a part of the invention.

9 Claims, 14 Drawing Sheets

Fenugreek/Luteolin Comparison by HPLC

Overlay Chromatographic Trace of Fenugreek and Luteolin Injections

Photomicrograph showing histologically normal liver of a
mildly diabetic rabbit treated for 30 days.
(H&E x 200)

Photomicrograph showing vacuolated nuclei in the liver parenchyma cells with chromatin pushed towards one side in an untreated, mildly diabetic rabbit.
(H&E x400)

Photomicrograph showing fatty infiltration in the myocardium of untreated, severely diabetic rabbit.
(H&E x200)

Photomicrograph showing fatty infiltration in the pancreatic tissue
of an untreated, severly diabetic rabbit.
(H&E x 200)

Photomicrograph showing histologically normal pancreatic tissue
of a severely diabetic rabbit treated for 30 days.
Islet cells are clearly visible.
(H&E x400)

Photomicrograph showing vacuolated cells in the renal tubules and hyalinized material in the glomeruli in the kidney of an untreated, severely diabetic rabbit.
(H&E x400)

Photomicrograph showing areas of calcification in and
around the renal tubules in the kidney of an
untreated, severely diabetic rabbit.
(H&E x200)

Photomicrograph showing histologically normal kidney of a
severely diabetic rabbit treated for 30 days.
(H&E x200)

Photomicrograph showing subcapsular scarring in the renal tissue
of an untreated, mildly diabetic rabbit.
(H&E x200)

Photomicrograph showing histologically normal kidney of a
mildly diabetic rabbit treated for 30 days.
(H&E x200)

ANTI-DIABETIC AND CHOLESTEROL LOWERING PREPARATION FROM FENUGREEK SEEDS

The present application is a Continuation Application of 10/117,444 filed Apr. 4, 2002 now abandoned.

TECHNICAL FIELD

This application claims the benefit of priority from co-pending U.S. Provisional Application Ser. No. 60/282,272, filed Apr. 5, 2001. This invention relates to natural compositions having biologically useful activities and, more particularly to a composition having blood glucose-lowering or cholesterol-lowering activity obtained from Fenugreek seed.

BACKGROUND

Hyperglycemia and hypercholesterolemia are major health concerns. Hyperglycemia can be due to diabetes, of which there are two major types—insulin dependent diabetes mellitus (IDDM), or type I diabetes, and non-insulin dependent diabetes mellitus (NIDDM), or type II diabetes. IDDM, or juvenile onset diabetes, is found mostly in young patients and is believed to be caused by genetically destructive mechanisms involving circulating antibodies to insulin which are aggravated by external factors such as infection (viruses, etc.), toxic chemicals, etc. As the name suggests, insulin is required for the treatment of IDDM.

NIDDM, or maturity onset diabetes, is more common than IDDM, and occurs mostly in adults, either obese or non-obese. In NIDDM there is a deficiency of insulin secretion or action. This deficiency may be due to down regulation of insulin receptors, decreased sensitivity to insulin action or a post receptor defect in which the insulin signal is inefficiently or improperly transduced. About 70% of diabetics have NIDDM and require oral antidiabetic drugs, either alone or in combination with insulin.

Insulin is typically required to be injected and is used for diabetics with insulinopenia who do not respond to diet, oral drugs, or both. Some of the possible side effects of insulin use are insulin antibody formation, insulin resistance, or allergic symptoms. Oral drugs for diabetes are generally of two types: biguanides and sulphonylureas. These drugs are referred to as hypoglycemic drugs because they decrease blood glucose levels in diabetic patients. Oral drugs differ from insulin in their chemical structure and their mechanism of action.

Their primary mechanism of blood glucose-lowering action is extra-pancreatic, i.e., they function by increasing the utilization of glucose in tissues (e.g., liver and muscle), decreasing the formation of glucose (gluconeogenesis) in liver, and reducing the absorption of glucose from intestines. The increased utilization of glucose caused by biguanide drugs, especially phenformin, produces lactic acid which can cause lactic acidosis, a serious side effect. For this and other reasons, phenformin has been discontinued from use in some countries, but is used occasionally in some other countries.

Particular examples of earlier sulphonylureas are tolbutamide (orinase), chlorpropamide, acetohexamide (dymelor), and tolazamide (tolinase). Their primary mechanism of action is to increase the release of insulin from the pancreatic beta cells in the islets of Langerhans, which, in turn, reduces blood glucose levels. Sulphonylureas are also known to act on tissues other than the pancreas (extrapancreatic effect), like the liver. Many of these drugs have been replaced by more potent second-generation sulphonylureas, like glibenclamide, gliclazide, glitazones and glipizide. The latter drug has a longer duration of action, up to 24 hours.

Because of its higher potency, glibenclamide treatment frequently produces hypoglycemia (decrease in blood glucose level below normal). Furthermore, second-generation sulphonylureas also produce serious side effects including myocarditis (in some obese diabetics), hyponatremia, transient leukopenia, and thrombocytopenia. Long-term use of these drugs over a number of years, taken daily or more than once in a day, is associated with hypoglycemia or hyperglycemia, diabetic ketoacidosis, and may cause coma, allergic reactions, leukopenia, skin and gastrointestinal disturbances and predispose to coronary artery disease. Furthermore, long-term use often necessitates increased doses to achieve efficacy. Daily injection of insulin, besides being painful, may cause depression and other psychological problems.

Hypercholesterolemia can lead to cardiovascular disease (CVD) which accounts for a major proportion (23%) of all deaths. Atherosclerosis, together with its other complications, is the pathological process that underlies the majority of coronary heart diseases (CHD). Atherosclerosis is also responsible for thrombotic and embolic strokes, aortic aneurymal disease, renovascular hypertension, peripheral vascular diseases, and other clinical syndromes. Therefore, prevention of atherosclerosis is of paramount importance for increasing human life span and for improving health.

Dietary habits contribute to the increased incidence of coronary and other atherosclerotic diseases. In particular, the intake of saturated fat and cholesterol (Stamler et al., 1988, *Arch. Pathol. Lab. Med.* 112:1032) along with high calories, as well as a low fiber intake lead to high levels of total serum cholesterol and its atherogenic subfractions (low-density lipoproteins (LDL) and very low density lipoproteins (VLDL)), and to high prevalence and incidence rates of hypercholesterolemia. Increased serum cholesterol is one of the major etiologically significant risk factors for CHD and other atherosclerotic diseases.

*Trigonella foenumgraecum* Linn, commonly known as fenugreek, belongs to the family Papilinaceae Leguminosae. It is an annual herb growing to a height of about one foot. The seeds of this plant are used as spice in India and many other countries. Fenugreek seeds are 2-5 mm long and 2-6 mm broad with yellowish brown color and have a furrow on both sides (see FIG. 1). The seeds contain proteins (13%), fat (26%), fiber (46%), carbohydrates (7%), vitamins (3%) mostly carotene, thiamine, riboflavin and nicotinic acid, minerals (4%) and other saponins (steroidal & non steroidal).

Medicinal properties have been attributed to this plant. Administration of whole seed powder purportedly prevented hyperglycemia induced by cadmium and alloxan in rats. T. Ghafghazi et al., *Shiraz Med. J.*, 8, 14-25 (1977). Powder from seeds taken every day for 10 days reduced fasting blood glucose levels and improved glucose tolerance in Type I diabetic patients. R. D. Sharma et al., *Eur. J. Clin. Nutr.*, 44(4), 301-306 (1990). Seed powder was also asserted to have hypocholesterolemic effect. Y. Sauvaire et al., *Lipids*, 26(3), 191-197 (1991). These hypoglycemic and hypocholesterolemic activities have been attributed to either fiber or saponins. Coumarin, a minor component of fenugreek seeds, showed hypoglycemic effect; however, coumarin is toxic at all doses tested. Decoction of the seeds (boiling in water) purportedly improved severe diabetes and cured milder diabetes in humans. M. Moissides et al., *Janus* 43, 129-13 (1979).

SUMMARY

The invention provides methods for obtaining a composition having blood glucose-lowering or cholesterol-lowering activity from Fenugreek seed or seed part. In one embodiment, a method includes producing an aqueous extract by contacting Fenugreek seed or seed part with an aqueous solution (e.g., water or a non-organic buffer), the solution having less than about 50% ethanol (40%, 30%, 20%, 10%, 5%, or less); and fractionating the aqueous extract to enrich for a component(s) having blood glucose-lowering or cholesterol-lowering activity and to remove a blood glucose-increasing activity, thereby obtaining a composition having blood glucose-lowering or cholesterol-lowering activity without substantial blood glucose-increasing activity. In one aspect, the fraction comprises fractionating by chromatography (e.g., ion exchange, such as anion exchange). In one embodiment, the anion exchange chromatography comprises DEAE-cellulose chromatography.

Additional methods of obtaining a composition having blood glucose-lowering or cholesterol-lowering activity from Fenugreek seed or seed part include further fractionating the first fractionated composition. In one embodiment, a composition having blood glucose-lowering or cholesterol-lowering activity from Fenugreek seed or seed part is further fractionated by gel filtration (e.g., sephadex G 100 chromatography). In another embodiment, a composition having blood glucose-lowering or cholesterol-lowering activity is further fractionated by thin layer chromatography using, for example, a low molecular weight alcohol (e.g., n-butanol), acid and water solvent (in a ratio of about 5:1:4 volume/volume).

Methods of the invention can employ seed or seed part (germ, etc.) that has been dried or has some moisture content (e.g., less than about 25%, 15%, 10%, 5%, or less). Methods of the invention and compositions thus obtained also include those of germinated seed, or germinated seed or seed a part thereof.

Extract can be produced by soaking Fenugreek seed or seed part in an aqueous solution for at least about 2 hours, 4 hours, 8 hours, 12 hours, or more. The extraction is performed at a temperature below about 25 degrees C., about 4 to about 8 degrees C.

The invention also provides compositions having blood glucose-lowering or cholesterol-lowering activity. In one embodiment, a composition of the invention having blood glucose-lowering or cholesterol-lowering activity has one or more active components from Fenugreek seed or seed part. In another embodiment, a composition of the invention is produced using a method of the invention. Such compositions having blood glucose-lowering or cholesterol-lowering activity produced in a method of the invention include FII, GII and III. Compositions substantially the same as compositions produced by methods of the invention also are provided. In one embodiment, a composition is characterized as soluble in water; insoluble in organic solvent; and having a component with an absorption maximum of about 270 nm and about 340 nm in 0.1 N HCl. In additional embodiments, a composition is further characterized as having an active component with a molecular weight of less than about 500 Daltons, or an Rf value of about 0.60 to about 0.65 on a TLC silica gel G plate having a mobile phase of alcohol, acid and water in a ratio of about 5:1:4 volume/volume. In yet other embodiments, a composition is further characterized as having a minor active component with an Rf value of about 0.80 to about 0.85 on a TLC silica gel G plate having a mobile phase of alcohol, acid and water in a ratio of about 5:1:4 volume/volume The compositions of the invention are further characterized by their activity, for example, in one embodiment, a composition reduces by about 20% or more blood glucose in an animal 2 hours after administering about 50 mg/kg of the composition to the animal. In another embodiment, a composition reduces by about 20% or more blood glucose in an animal 1 hour after administering about 50 mg/kg of the composition to the animal.

The invention also provides compositions having blood glucose-lowering or cholesterol-lowering activity further comprising a pharmaceutically acceptable formulation.

In one embodiment, a pharmaceutical formulation of the invention comprises a pill, a capsule, a syrup or an elixir. Thus, the compositions of the invention include those suitable for oral administration so as to be useful in practicing a method of the invention, for example.

The invention further provides methods for treating a subject in which it is desirable to produce one or more activities of an invention composition. In one embodiment, a method for increasing blood insulin in a subject (e.g., by increasing release of insulin from the pancreas) includes administering to a subject an amount of an invention composition effective to increase the amount of blood insulin in the subject. In another embodiment, a method for decreasing blood glucose in a subject (e.g., extra-pancreatic; by increasing cellular uptake of glucose or increasing metabolism of glucose) includes administering to a subject an amount of an invention composition effective to decrease glucose in the subject's blood. In yet another embodiment, a method for improving glucose tolerance in a subject includes administering to a subject an amount of an invention composition effective to improve glucose tolerance in the subject.

The invention additionally provides methods for treating, preventing or ameliorating a condition in a subject, the condition treatable by an activity of an invention composition. In one embodiment, a method for treating a subject having or at risk of having a hyperglycemic condition includes administering an amount of an invention composition effective to ameliorate the hyperglycemic condition in the subject. In one aspect, the hyperglycemic condition is diabetes (e.g., insulin-dependent (IDDM) or non-insulin-dependent (NIDDM) diabetes or severe diabetes).

The invention also provides methods for treating hyperglycemic conditions associated with, caused by, or at an increased risk due to diabetes. Such conditions include ischemic cerbrovascular disease or stroke, brain infarction, postischemic brain injury, diabetic retinopathy (eye damage), neuropathy (autonomic), nephropathy (kidney damage), skin infections and other cutaneous disorders, slow healing of injuries or wounds, diabetic carbuncles, cataracts, diabetic foot and accelerated periodontitis.

In additional embodiments, methods for reducing sorbitol dehydrogenase or aldose reductase activity in kidney are provided. A method of the invention includes administering to a subject an amount of an invention composition effective to reduce sorbitol dehydrogenase or aldose reductase activity in a kidney of the subject. In yet another embodiment, a method for increasing superoxide dismutase or glutathione peroxidase activity in a subject, includes administering to a subject an amount of an invention composition effective to increase superoxide dismutase or glutathione peroxidase activity in the subject.

Methods for treating a subject having or at risk of having a hypercholesterolemic condition also are provided. In one embodiment, a method for decreasing blood cholesterol or triglycerides in a subject includes administering an amount of an invention composition effective to decrease blood cholesterol or triglycerides in the subject. In another embodiment, a method for inhibiting increases in blood cholesterol or triglycerides in a subject includes administering an amount of an invention composition effective to inhibit increases in blood cholesterol or triglycerides in the subject. In yet another embodiment, a method for improving serum lipid profile in a subject includes administering an amount of an invention composition effective to decrease blood cholesterol or triglycerides in the subject. In still another embodiment, a method for treating a subject having or at risk of having an undesirable or excessive amount of cholesterol includes administering an amount of an invention composition effective to lower cholesterol in the subject.

The invention further provides methods for treating, preventing, or ameliorating a condition in a subject associated with or that results from a hyperglycemic or hypercholesterolemic condition. In one embodiment, a method for preventing a histopathological change associated with a chronic or acute hyperglycemic condition includes administering to a subject an amount of an invention composition effective to prevent the histopathological change associated with the chronic or acute hyperglycemic condition in the subject. In another embodiment, a method for ameliorating or reversing a histopathological change associated with a chronic or acute hyperglycemic condition includes administering to a subject an amount of an invention composition effective to ameliorate or reverse the histopathological change associated with the chronic or acute hyperglycemic condition in the subject. Histopathological changes treatable include those of the pancreas, kidney, liver, eye, or cardiovascular system. Accordingly, a method for ameliorating sclerosis in a subject includes administering an amount of an invention composition effective to ameliorate sclerosis in the subject (e.g., reduction of plaque or intimal thickening of a blood vessel, such as an artery or vein, or a tissue, such as liver).

The invention also provides dosage amounts of an invention composition appropriate for use in the methods of the invention, such as a dose of about 25 to about 50 mg composition/kg subject mass, about 50 to about 100 mg composition/kg subject mass and about 100 to about 200 mg composition/kg subject mass. Invention compositions can be administered as a single dose, administered daily or intermittently (e.g., once every 2, 3, 4, 5, 6, 7, 8, 9 or 10 days) in the methods of the invention. The compositions of the invention can be administered prophylactically to a subject in the methods of the invention.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
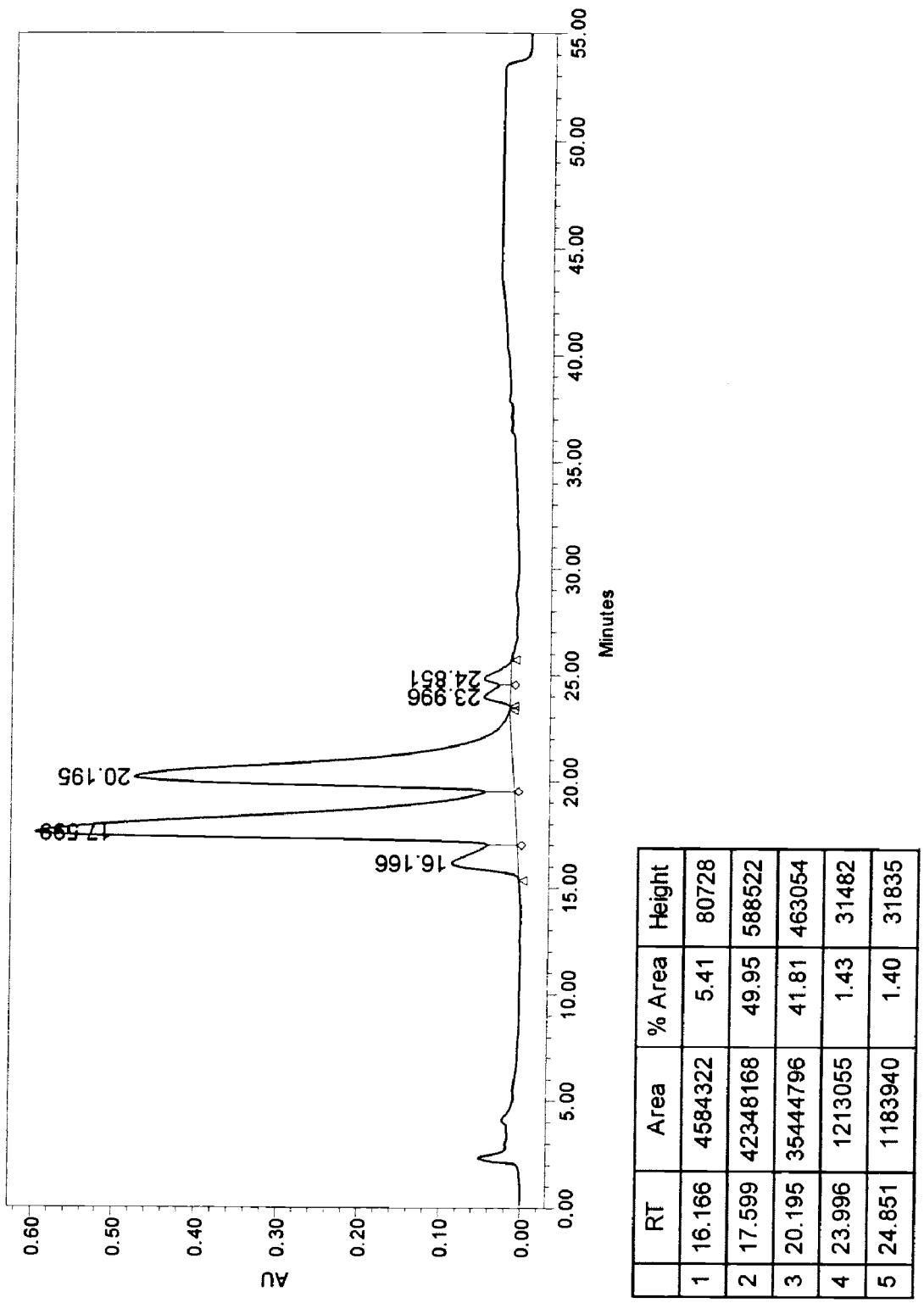
FIG. 1 is a photomicrograph of liver of a severely diabetic rabbit.

The present invention is based, in part, on the isolation of a composition from Fenugreek seed having glucose-lowering and cholesterol-lowering activity in vivo. The composition includes one or more components that confer glucose-lowering or cholesterol-lowering activity. Thus, the composition is useful for decreasing blood glucose, improving glucose tolerance, decreasing cholesterol or improving serum lipid profile in a subject and for treating physiological conditions/pathologies associated with undesirable levels of glucose or cholesterol, glucose intolerance or hypersensitivity, and poor serum lipid profile. In addition, the composition has other activities which indicate applicability in treating other disorders. For example, the composition increases superoxide dismutase and/or glutathione peroxidase enzyme. Thus, the composition is also useful for reducing inflammation or cell injury or tissue damage resulting from free radical production, as well as reducing mutagenesis which can lead to hyperplasia and/or cancer, due to it ability to reduce the amount of free radicals in a subject that cause tissue damage or contribute to cell hyperplasia, cancer initiation or development, or tumor promotion.

For example, a patient with excessive or undesirable blood glucose levels (e.g., hyperglycemic) or with excessive or undesirable cholesterol levels (e.g., hypercholesterolemic) can be treated with the composition, or a component present within the composition, to decrease blood glucose or cholesterol levels. Decreased levels of blood glucose or cholesterol resulting from administering the composition can prevent, inhibit, or ameliorate some or all of the symptoms or pathologies associated with excessive or undesirable amounts of blood glucose or cholesterol (e.g., diabetes, familial hypercholesterolemia, heart disease, etc.). Thus, in accordance with the invention, there are provided methods for decreasing blood glucose, improving glucose tolerance, decreasing cholesterol and improving serum lipid profile.

The invention also provided methods for obtaining a composition having blood sugar-(e.g., glucose) lowering or cholesterol-lowering activity. In one embodiment, a method of the invention includes producing an aqueous extract by contacting Papilinaceae Leguminosae seed or seed part with an aqueous solution having less than about 50% ethanol; fractionating the extract to enrich for a component(s) having blood glucose-lowering or cholesterol-lowering activity to remove a blood glucose increasing activity, thereby obtaining a composition having blood glucose-lowering or cholesterol-lowering activity without substantial blood glucose-increasing activity. In one aspect, the aqueous extract is obtained by contacting Fenugreek seed or seed part.

The composition having blood glucose-lowering or cholesterol-lowering activity can be obtained from Fenugreek seed or seed part. Fenugreek is a member of the Papilinaceae Leguminosae plant family. Accordingly, it is contemplated that the composition can be obtained from seed or seed part of any plant within this family.

The composition having blood glucose-lowering or cholesterol-lowering activity can also be obtained from a seed at any stage of development (immature or mature or germinating or germinated), or a seed part, including, for example, the embryo, the endosperm and the surrounding layers (e.g., coat). Those skilled in the art will know of methods to separate various parts of the seed to use as material to obtain an invention composition. Seed or seed parts include germinated seed. Germinated seed or seed part are typically from seeds germinated for 1 to 3, 1 to 5, 1 to 10 or 1 to 20 days, or even longer, more typically from 1 to 3 days. Furthermore, seeds or seed parts having any amount of moisture content, or none for that matter, germinated or non-germinated, are contemplated as material useful for obtaining an invention composition. Thus, moisture content is not to be construed as limiting the seed or seed part used to obtain the composition. Typical seed moisture content ranges from about 5% to 30%, more typically 5% to 25%, most typically, 5% to 15%.

The aqueous extract can be produced by contacting Papilinaceae Leguminosae seed with an aqueous solution such as water for a period of time. In one embodiment, Papilinaceae Leguminosae seed is soaked in an aqueous solution for at least about 2 hours. In another embodiment, Papilinaceae Leguminosae seed is soaked in an aqueous solution for at least about 4 hours. In yet another embodiment, Papilinaceae Leguminosae seed is soaked in an aqueous solution for at least about 8 hours. In still another embodiment, Papilinaceae Leguminosae seed is soaked in an aqueous solution for at least about 12 hours.

Temperatures typically used during preparation of an invention composition from seed range from about 4 to about 30° C. More likely, the temperature ranges between about 4 and 25° C., even more likely, between about 4 and 20° C., and most likely between about 4 and 15° C., or between about 4 and 10° C. For longer extraction time periods (e.g., greater than 8 hours), between about 4 and 15° C., or between about 4 and 10° C. prevents excess loss of activity.

If desired, the seed or seed part can be moistened, rehydrated, or presoaked prior to extracting. For example, seed can be presoaked in a solution (aqueous or organic), the presoak solution removed, and then the presoaked seed or seed part soaked in an aqueous solution to produce the aqueous extract.

As used herein, the term "aqueous solution" refers to a liquid whose composition is about 50% or more water by volume. Typically, the aqueous solution will have greater than about 60% water, for example, 70%, 80%, 90% or 100% water. In one embodiment, the aqueous solution has less than about 50% ethanol. In another embodiment, the aqueous solution has less than about 40% ethanol. In yet another embodiment, the aqueous solution has less than about 30% ethanol. In other embodiments, the aqueous solution has less than about 20%, 10%, 5%, or less ethanol.

The aqueous solution can contain additional miscible or immiscible components. For example, an aqueous solution can have buffering agents or salts, to stabilize the pH. Particular examples of buffers are phosphate and HEPES buffers which can have a stabilized pH, such as a pH in a physiological range between about pH 6.0 and about pH 8.0. Organic solvent (e.g., phenol, hexane, acetone etc.) can be present in the aqueous solution for the purpose of removing impurities or contaminants, before, during or after extraction. For example, an organic solvent such as phenol can be mixed with the aqueous extract and separated from the aqueous solution by allowing the phases to partition. The apparent solubility properties of the composition having blood glucose-lowering or cholesterol-lowering activity favor partitioning of the composition in the aqueous phase. The aqueous solution or aqueous extract can additionally contain solids, such as activated carbon, diatomaceous earth, alumina and the like, salts, chelating agents, preservatives and stabilizing agents, which can be useful for removing impurities, increasing the amount of glucose-lowering or cholesterol-lowering composition extracted from Papilinaceae Leguminosae seed or part, or stabilizing or preventing degradation of the composition, for example.

As used herein, the phrases "without substantial," "substantially without," or "substantially devoid" means that the component referred to by the phrase is present in a relatively small amount or is completely absent. In the case of a blood glucose increasing activity, i.e., "without substantial blood glucose-increasing activity," this phrase means an amount of blood glucose-increasing activity that does not significantly reduce a glucose-lowering or insulin-increasing activity. Typical amounts of blood glucose increasing activity present prior to fractionation reduce glucose-lowering activity from about 50-100%. Significant reductions in glucose-lowering activity typically are greater than about an 80% reduction of the blood glucose-decreasing activity. Thus, when the amount of blood glucose increasing activity present prior to fractionation reduces glucose-lowering activity by 100% (i.e., there is no blood glucose lowering activity present), about 20% or more of the blood-glucose increasing activity is removed. When the amount of blood glucose increasing activity present prior to fractionation reduces glucose-lowering activity by 50%, about 10% or more of the blood-glucose increasing activity is removed. More likely, blood glucose-increasing activity is less than about 70% of the total activity, most likely less than about a 60% of the total activity, or less (e.g., less than about 50%, 40%, 30%, 20%, 10% or less of activity, such as 5% or 0%).

Thus, in a composition of the invention, there may be moderate amounts of glucose-increasing activity remaining after fractionation. The amount present will generally be less than about 25% (by mass) of the total (i.e., the combined mass of glucose-lowering composition and glucose-increasing component(s)). Typically, the amount will be less than about 20%, more typically, less than about 10% and most typically less than about 5%, for example, 4%, 3%, 2%, 1% or 0%. The amount of glucose-increasing activity present in a particular preparation of an invention composition can be determined by testing the composition using the assays disclosed herein, and comparing activity to an invention composition in which glucose-increasing component has been completely removed, or its amount is known. In the therapeutic methods of the invention, it is likely that the amount of glucose-increasing component(s) in the composition will not prevent or substantially interfere with glucose-lowering activity or cholesterol-lowering activity of the invention.

Thus, in a step of fractionating the extract to enrich for a component having blood glucose-lowering or cholesterol-lowering activity, the fractionated extract can contain an amount of glucose-increasing activity. In one embodiment, the amount of glucose-increasing activity remaining after fractionating the extract is about 80% of the total amount of glucose-increasing activity before fractionating the extract (i.e., where blood glucose increasing activity is 100% prior to fractionation, 20% of the glucose-increasing activity has been removed by fractionation). In another embodiment, the amount of glucose-increasing activity remaining after fractionating the extract is about 70% of the total amount of glucose-increasing activity before fractionating the extract (i.e., where blood glucose increasing activity is 100% prior to fractionation, 30% of the glucose-increasing activity has been removed). In yet another embodiment, the amount of glucose-increasing activity remaining after fractionating the extract is about 60% of the total amount of glucose-increasing activity before fractionating the extract. In still yet another embodiment, the amount of glucose-increasing activity remaining after fractionating the extract is about 50% of the total amount of glucose-increasing activity before fractionating the extract. In various additional embodiments, the amount of glucose-increasing activity remaining after fractionating the extract is about 40%, 30%, 20%, 10%, 5% or less, of the total amount of glucose-increasing activity before fractionating the extract.

The aqueous extract can be fractionated using any of a variety of purification procedures known in the art, so long as some amount of glucose-increasing activity is removed from the composition having blood glucose-lowering or cholesterol-lowering activity. In one embodiment, a method of the invention includes fractionating by chromatography. In one aspect, the chromatography is by anion exchange. In another aspect, the chromatography is by weak anion exchange. In yet another aspect, the chromatography is by DEAE-cellulose. In still other aspects, the chromatography is by DEAE-sephadex or amberlite IR100. In another embodiment, the protein in the extract can optionally be precipitated with full saturation ammonium sulfate, precipitated proteins removed, and the supernatant dialyzed or passed through DEAE-cellulose to remove ammonium sulfate.

Other molecular fractionation procedures applicable in the methods of the invention include size-based molecular fractionation, for example, size exclusion by gel filtration or by membrane filtration using a membrane having pore sizes through which only molecules having less than a certain size may pass, gel electrophoresis and sucrose gradient centrifugation. Fractionation techniques useful in a method of the invention also include techniques that separate molecules on the basis of physical or chemical characteristics (e.g., hydrophobicity, hydrophilicity, polarity, affinity, etc.), which include, for example, thin layer chromatography (TLC), cation exchange (strong or weak), reverse phase, hydrophobic interaction, and affinity (metal-chelate, antibody, ligand, receptor, nucleic acid, etc.). Fractionating the extract to obtain a composition having blood sugar-lowering or cholesterol-lowering activity can be performed with any of a variety of established techniques known in the art; appropriate media for such fractionations are commercially available (see, e.g., Remington's Pharmaceutical Sciences (1990) 18th ed., Mack Publishing Co., Easton, Pa.; Pharmacia Biotech BioDirectory '96).

The active fraction(s) can be identified using the in vitro and in vivo methods disclosed herein, as well as by using the various physical and spectral characteristics described herein. The fractionated composition is typically greater than about 60% pure, more likely, 70%, 80%, 90%, or more pure. Purity of the fraction can be determined by TLC, HPLC, or spectroscopy (UV or visible, see, e.g., Example 2).

If desired, multiple fractionations can be performed. Thus, in another embodiment, a method of the invention includes additional fractionations (i.e., two or more). In one aspect, the composition obtained after a first fractionation is further fractionated by gel filtration chromatography. In another aspect, the composition obtained after a first fractionation is further fractionated by SEPHADEX chromatography (e.g., SEPHADEX G-25, G-100). In yet another aspect, the composition obtained after a first fractionation is further fractionated by TLC. In one aspect, the TLC fractionation employs a low molecular weight alcohol (e.g., n-butanol), acid and water solvent (e.g., in a ratio of about 5:1:4). In yet another embodiment, the composition obtained after a first fractionation is further fractionated by HPLC.

It may be desired to change the volume of liquid or alter the buffer in a method of the invention. For example, before fractionating the aqueous extract, it may be desired to reduce the volume of liquid. To reduce the volume of liquid, the material in the extract can be precipitated, for example, by adding a liquid in which the composition is insoluble. For example, an equal or greater volume of ethanol or methanol can be added to the liquid to precipitate the composition. Alternatively, the composition can be lyophilized using vacuum. The precipitate can be resuspended in a solution of the desired volume have buffering components appropriate for the fractionation, for example. As an alternative, in order to change solution volume or alter buffer, dialysis can be performed.

A composition of the invention may contain a single component that has all of the hypoglycemic, hypocholesterolemic, and other activities described herein (e.g., reversing histopathological changes, increasing antioxidant enzymes, etc.). Alternatively, there may be multiple molecules (i.e., subcomponents) present within the composition, each of which has one or more of the activities. The sum of the components would therefore account for the activities described herein.

Metabolites or intermediates of the composition and subfractions of the composition having one or more of the activities disclosed herein are also included. The metabolites or intermediates may be produced by the body's detoxification system (e.g., cytochrome P450 enzymes, etc.) in order to facilitate their elimination. Active metabolites, intermediates, and subfractions can be identified as having structural similarity to an invention composition or an active component therein by using the activity assays described herein, for example. Active metabolites or intermediates of an invention composition, or any active subcomponent thereof or subfraction, are useful in the methods of the invention, for example, treating a subject in which it is desired to produce one or more of the activities described herein. Such intermediates and metabolites can be produced by incubating a composition of the invention with gastric juice (natural or artificial) in vitro, for example, or in a liver homogenate. The composition, any subcomponent, any active metabolite or intermediate, and any subfraction, having one or more of the activities described herein are useful for treating a subject having hyperglycemia, hypercholesterolemia, or others described herein or known in the art.

A method of the invention including single or multiple fractionations each produce a composition having blood glucose-lowering activity or cholesterol-lowering activity without substantial glucose-increasing activity. For example, as shown in Flow Chart 1, fractionating the aqueous extract by chromatography (DEAE-cellulose) produces an active yellow fraction, referred to herein as "Product 1," "Menthi FII," or simply "FII" having blood glucose-lowering and cholesterol-lowering activity. FII is mixture of water-soluble compounds from fenugreek in which component(s) that increases blood glucose appears to be entirely or mostly absent. This compound also improves glucose tolerance, increases insulin levels, and improves serum lipid profile.

"Product 2," "Menthi GII" or simply "GII" is produced after fractionating of FII by Sephadex (G100) chromatography. GII appears to be highly purified and almost homogenous (see FIG. 2). This compound has, inter alia, blood glucose-lowering activity, improves glucose tolerance, increases insulin levels, and improves serum lipid profile. GII is highly potent when compared with other drugs. For example, a dose of 50 mg/kg body weight is useful even in ameliorating severe diabetes (see, e.g., Example III, Table 4; Example VII, Table 11). In addition, after treatment with GII, fasting blood glucose levels returned to nearly normal value in diabetic and severely diabetic rabbits. Even after drug therapy was ceased, fasting blood glucose level was maintained at a lower level for nearly ten days, indicating prolonged efficacy.

Fractionation of GII by thin layer chromatography produced one and sometimes two spots. A single large spot was active and is referred to herein as TII. This compound also has, inter alia, blood glucose-lowering activity, improves glucose tolerance, increases insulin levels, and improves serum lipid profile. Accordingly, the invention provides at least one substantially purified component (i.e., greater than about 90% or more) having one or more of the activities (e.g., blood glucose-lowering), and other characteristics described herein.

Thus, in accordance with the invention, further provided are compositions having blood glucose-lowering or cholesterol-lowering activity without substantial blood glucose-increasing activity. In one embodiment, the composition is free of glucose increasing activity. In another embodiment, the composition is referred to as FII. In yet another embodiment, the composition is referred to as GII. In still another embodiment, a composition is referred to as TII. FII, GII and TII compositions have one or more of the activities or physical characteristics described herein. The invention compositions, including FII, GII and TII are useful in the methods of treatment, as described herein.

A composition of the invention has one or more of the activities (e.g., blood glucose-lowering or cholesterol-lowering activity) or physical characteristics described herein.

Particular examples of physical characteristics of a composition are a molecular weight of less than about 500 daltons, soluble in water, insoluble in organic solvent, has an absorption peak of about 211 nm in alkali solution and 340 nm in acid, and has an Rf value of about 0.65 on a TLC silica gel G plate having a mobile phase of alcohol (n-butanol), acid, and water in a ratio of about 5:1:4 volume/volume.

In additional embodiments, the composition is characterized by its functional activity (e.g., glucose-lowering activity, insulin increasing activity, cholesterol-lowering activity, improving serum lipid profile activity, etc.) in animals (e.g., mammals). For example, in one embodiment, the composition reduces by about 20% or more blood glucose in an animal 2 hours after administering about 100 mg/kg bodyweight (b.w.) of the composition to the animal. In another embodiment, the composition reduces by about 20% or more blood glucose in an animal 2 hours after administering about 50 mg/kg bodyweight of the composition to the animal. In yet another embodiment, the composition reduces by about 20% or more blood glucose in an animal 2 hours after administering about 25 mg/kg bodyweight of the composition to the animal. In still another embodiment, the composition reduces by about 20% or more total cholesterol in a diabetic or severely diabetic animal 2 hours after administering about 50 mg/kg bodyweight of the composition to the animal. Typically, reduction in blood glucose or cholesterol levels will be 20% or more, for example, 30%, 50%, or 60%, or more.

An invention composition has "glucose-lowering activity" in animals, which means a reduction in the amount of sugar (i.e., glucose) present in the blood stream of an animal. An invention composition also produces, directly or indirectly, via a pancreatic or extra-pancreatic pathway, other hypoglycemic effects. For example, a composition of the invention improves glucose tolerance and increases insulin levels in subdiabetic, diabetic, and severely diabetic animals (see, e.g., Tables 2-6; Table 10).

In addition to decreasing blood glucose, an invention composition, directly or indirectly produces, via a pancreatic or extra-pancreatic pathway, other hypoglycemic activities. For example, an invention composition increases insulin levels and improves glucose tolerance in animals. An invention composition increases the number of islet cells (regenerate) of the pancreas (see, e.g., Example IX, Table 13, FIGS. 7 and 8) or improves their function (i.e., increase insulin production or release). An invention composition also stimulates activity or increases levels of enzymes of glucose utilization in glycolysis, HMP and other pathways (e.g., glucokinase), in tissue of the body, and decreases glucose formation (gluconeogenesis enzymes and enzymes of the polyol pathway) or activity or levels of enzymes (e.g., glucose-6-phosphatase, aldose reductase, sorbitol dehydrogenase) in these pathways (see, e.g., Tables 12 and 13). A composition of the invention normalizes levels of malic enzyme. The extra-pancreatic activity of an invention composition is corroborated by decreased fasting blood glucose in severely diabetic rabbits that have little if any pancreatic function (see, e.g., Table 4).

Thus, in accordance with the invention, there are provided methods for decreasing blood sugar, for increasing insulin, for improving glucose tolerance, for increasing the number or improving the function of pancreatic islet cells, for increasing activity of enzymes of glucose utilization, for decreasing activity or levels of enzymes of glucose formation. In one embodiment, a method of the invention includes administering to a subject an amount of the composition having blood sugar-lowering or cholesterol-lowering activity effective to decrease blood sugar of the subject. In another embodiment, a method of the invention includes administering to a subject an amount of the composition effective to increase the amount of insulin in the blood of the subject. In yet other embodiments, an amount of the composition effective to improve glucose tolerance, or to increase the number or improve the function of pancreatic islet cells, to increase activity or levels of enzymes of glucose utilization, to decrease activity or levels of enzymes of glucose formation, is administered to the subject.

As disclosed herein, an invention composition has, inter alia, cholesterol-lowering activity. The phrase "cholesterol-lowering activity" means a reduction in total blood cholesterol. The phrase therefore includes a decrease in VLDL or LDL, which contain varying amounts of cholesterol. A composition of the invention also can reduce blood triglycerides and increase HDL (see, e.g., Tables 16 to 19). The ability to reduce cholesterol, VLDL, LDL, and triglycerides is referred to herein as "improving serum lipid profile." Typically, the reduction of cholesterol, VLDL, LDL or triglycerides will be at least about 10%. More typically, the reduction will be 20% or more, for example, 30%, 50%, 60%, 80%, or 100% or more (e.g., 200).

Thus, in accordance with the invention, there are provided methods of decreasing blood cholesterol, triglycerides, VLDL or LDL, and for increasing HDL. In one embodiment, a method of the invention includes administering to a subject an amount of the composition having blood glucose-lowering or cholesterol-lowering activity effective to decrease blood cholesterol in the subject. In another embodiment, a method of the invention includes administering to a subject an amount of the composition effective to decrease triglycerides in the subject. In yet other embodiments, an amount of the composition effective to decrease VLDL, LDL, and increase HDL (i.e., improve serum lipid profile) or decrease LDL oxidation or amount of oxidized LDL is administered to the subject.

Although the invention is not bound by any theory, the cholesterol-lowering activity of an invention composition may be linked to insulin-increasing activity. For example, the hypocholesterolemic activity of the composition may result from an ability to increase hormone-sensitive lipase activity, which degrades lipids, or decrease HMG-CoA reductase activity, an enzyme in the cholesterol biosynthesis pathway. Thus, hypocholesterolemic activity of an invention composition may be directly or indirectly linked to its hypoglycemic activity or, alternatively, be due to a direct or indirect effect on cholesterol biosynthesis or degradative pathways. Increased HDL likely results from a decrease in cholesterol, VLDL, LDL or triglycerides. As some cardiovascular diseases are due to oxidized LDL, it is likely that a composition of the invention inhibits LDL oxidation due to its antioxidant activity.

The term "subject" refers to an animal. Typically, the animal is a mammal, however, any animal (e.g., bird, reptile, etc.) having glucose, cholesterol or triglycerides present in blood is encompassed by the term. Particular examples of mammals are to primates (humans), dogs, cats, horses, cows, pigs, and sheep. A subject can be hyperglycemic or hypercholesterolemic, hyperglycemic and hypercholesterolemic, or neither hyperglycemic nor hypercholesterolemic.

A subject having or at risk of having a hyperglycemic or hypercholesterolemic condition, or an undesirable amount of blood glucose or cholesterol, or a pathology resulting from or associated with a hyperglycemic or hypercholesterolemic condition, chronic or acute, can therefore be treated by administering an invention composition. There are many chronic or acute hyperglycemic and hypercholesterolemic conditions that are associated with, create an increased risk of, or which result from hyperglycemia or hypercholesterolemia. Particular examples of hyperglycemic conditions treatable by a method of the invention include the various types of diabetes, for example, insulin-dependent, insulin-independent and severe diabetes. Hyperglycemic conditions associated with, caused by, or at an increased risk due to diabetes include, for example, ischemic cerbrovascular disease or stroke, brain infarction, postischemic brain injury, diabetic retinopathy (eye damage), neuropathy (autonomic), nephropathy (kidney damage), skin infections and other cutaneous disorders, slow healing of injuries or wounds, diabetic carbuncles, cataracts, diabetic foot and accelerated periodontitis.

Particular examples of hypercholesterolemic conditions treatable by a method of the invention include arteriosclerosis, coronary heart disease, hypertension, stroke, and blood vessel thrombosis. Thus, a subject can be administered an amount of the composition having blood glucose-lowering or cholesterol-lowering activity effective to ameliorate a hyperglycemic or hypercholesterolemic condition in the subject, such conditions including those described herein and others known in the art.

As disclosed herein, a composition of the invention decreases cholesterol and improves serum lipid profile of hypercholesterolemic animals (see, e.g., Tables 16-19). The improvement in serum lipid profile occurs without inducing hypoglycemia. Thus, in another embodiment, the invention provides methods for decreasing cholesterol and improving serum lipid profile in a subject without producing hypoglycemia in the subject. A method of the invention includes administering to a subject an amount of a composition having blood glucose-lowering or cholesterol-lowering activity sufficient to improve serum lipid profile without producing hypoglycemia in the subject.

A composition of the invention also prevents or reverses histopathological changes associated with hyperglycemia and hypercholesterolemia. For example, fat infiltration and fatty cysts present in liver of severely diabetic animals were absent in animals treated with GII (see, e.g., Example IX; compare also FIGS. 3 and 4 to FIG. 5). Fatty infiltration of the myocardium also was completely reversed in animals treated with GII. Improvements in pancreas function and histopathology were also evident in animals administered GII. For example, pancreas of severely diabetic animals revealed significant fatty infiltration and islet cells were either absent or few in number. Treatment reversed fatty infiltration and the number of islet cells either increased (i.e., regenerated; see, e.g., FIGS. 9 and 10) or their function improved, i.e., increased insulin production or release.

Thus, the invention also provides methods for preventing, inhibiting, and reversing histopathological changes associated with or that result from hyperglycemic and hypercholesterolemic conditions. A method of the invention includes administering an effective amount of a composition having blood glucose-lowering or cholesterol-lowering activity effective to prevent a histopathological change, improve a histopathological change, or reverse a histopathological change associated with or resulting from a hyperglycemic or hypercholesterolemic condition. In one embodiment, the improvement is in pancreas (e.g., increased function or number of islets, etc.). In another embodiment, the improvement is in kidney (e.g., decrease in calcification, fatty infiltration, etc.). In yet another embodiment, the improvement is in liver (e.g., decrease in fatty infiltration). In still another embodiment, the improvement is in blood vessel (e.g., decrease in plaque, such as in the aorta). In other embodiments, the improvement is in eye (e.g., decrease or an arrest of retinopathy, decrease in cataracts, improvement in vision), or wound or injury healing time (decreased), or diabetic foot. Free radicals are generated as a result of metabolic processes, which in turn, cause peroxidation of lipids. Lipid peroxidation products cause damage to many tissues in the body. Antioxidant defense mechanisms counteract these undesirable effects. An invention composition also has the ability, inter alia, to reduce the amount of free radicals produced in diabetes and which may account for complications associated with diabetes. For example, the level of antioxidant enzymes superoxide dismutase and glutathione peroxidase increase in diabetics treated with a composition of the invention (see, e.g., Table 14).

Thus, in accordance with the invention, also provided are methods of increasing antioxidant enzymes and decreasing free radicals. In one embodiment, a method of the invention includes administering an amount of an invention composition effective to increase glutathione peroxidase. In another embodiment, a method of the invention includes administering an amount of an invention composition effective to increase superoxide dismutase in a subject. In yet another embodiment, a method of the invention includes administering an amount of an invention composition effective to decrease free radicals in the body.

Free radicals can produce cellular and tissue damage, mutations of cellular components (e.g., DNA, protein) or, activate procarcinogens, which, in turn, can lead to various physiological conditions and pathological disorders. Such disorders can be produced by insufficient production of antioxidant enzymes, for example, superoxide dismutase or glutathione peroxidase, or undesirable or overproduction of free radicals during inflammation, for example. Thus, reducing free radicals in a subject or increasing antioxidant enzyme(s) can ameliorate a condition associated with the presence of free radicals in the subject.

Accordingly, the invention provides methods of ameliorating physiological conditions associated with free radicals. In one embodiment, a method of the invention includes administering to a subject an amount of an invention composition effective to ameliorate a pathological disorder associated with insufficient antioxidant enzyme production or expression. In another embodiment, a method of the invention includes administering to a subject an amount of an invention composition effective to ameliorate a pathological disorder associated with free radicals. Such disorders include, for example, cell injury or tissue damage produced by free radicals (e.g., iscehmia) during inflammation, as well as cell transformation due to mutagenesis caused by free radicals, which can lead to hyperplasia, cancer development or initiation, or tumor promotion.

As used herein, the term "ameliorate" means an improvement in the subject's condition, a reduction in the severity of the condition, or an inhibition of progression or worsening of the condition. In the case of a hyperglycemic condition (e.g., diabetes), for example, an improvement can be a decrease in blood glucose, an increase in insulin, an improvement in glucose tolerance, and improved pancreatic (e.g., islet cell) function. An improvement in a hyperglycemic condition also can include a decrease in a pathology associated with or resulting from the condition, such as an improvement in histopathology of pancreas (e.g., regeneration of islet cells that produce insulin), kidney (reduction or reversal of tubule calcification), liver or eye. In the case of a hypercholesterolemic condition (e.g., arteriosclerosis) resulting from excess blood cholesterol, triglycerides, VLDL or LDL, an improvement can be a decrease in blood cholesterol; triglycerides, VLDL or LDL, an increase in HDL, or a decrease in luminal thickening of a blood vessel (e.g., coronary artery). An improvement in a hypercholesterolemic condition also can include improvement in any of the various disorders well known in the art to be associated with hypercholesterolemia, for example, a decrease in intimal thickening of the coronary artery, fatty infiltration of myocardium or liver, hypertension (i.e., high-blood pressure), or thrombus formation or size.

An "effective amount" means the amount of an invention composition needed to produce a therapeutic effect or improvement in the condition. A therapeutic effect can be a small or moderate reduction of blood glucose or cholesterol levels, for example. Typical improvements can be a reduction of about 10%, 20%, 30% or more, for example, 40%, 50%, 60%, 70%, 80%, of blood glucose or cholesterol levels. Typical increases in insulin levels are about 10-20%, more typical, 30-40%, and most typical, 50-60% or more.

Doses that are sufficient to ameliorate hyperglycemia or hypercholesterolemia or pathologies associated with or that result from hyperglycemia or hypercholesterolemia, can be readily ascertained by the skilled artisan. Appropriate doses will depend upon the condition treated, the therapeutic effect desired, as well as the individual subject (e.g., whether the subject is hyperglycemic or hypercholesterolemic or not, the bioavailability within the subject, gender, age, etc.). Typically, the dose at which hypoglycemic activity is observed is in the range of about 10 to about 25 mg composition/kg subject mass, 25 to about 50 mg composition/kg subject mass, or about 50 to about 100 mg composition/kg subject mass. For example, as disclosed herein, administering the composition at low doses (e.g., 50 mg/kg subject mass) decreases blood glucose, increases insulin, and improves serum lipid profile. However, it is possible to administer greater doses (e.g., a dose of 100 to about 200 mg composition/kg subject mass or 200 to about 500 mg composition/kg subject mass daily), for example, in the case of a subject having severe or chronic hyperglycemia (e.g., severe diabetes) or hypercholesterolemia, or where a rapid blood sugar-lowering or cholesterol-lowering effect is desired.

The composition can be administered to the subject by any means appropriate for the condition to be treated. For example, the composition can be administered orally to inhibit or prevent acute or chronic hyperglycemia or hypercholesterolemia in a subject having or at risk of having acute or chronic hyperglycemia or hypercholesterolemia, for example, due to a genetic or other predisposing factor, such as an inability or deficiency in regulating blood glucose or cholesterol (e.g., familial hypercholesterolemia). Thus, in one embodiment, a composition is administered orally. A composition can be administered prophylactically to a subject prior to, development of symptoms associated with or resulting from the condition, for example, to prevent or inhibit hyperglycemia in diabetic subjects that occurs with age onset, exposure to high amounts of dietary glucose, or after glucose from food consumption, to prevent neuropathy, nephropathy, retinopathy, diabetic foot, cutaneous infection, diabetic cataracts, etc. Similarly, the composition can be administered prophylactically to a subject to decrease the risk of developing fatty deposits in tissues and organs, which lead to atherosclerosis and increased risk of stroke, for example. Moreover, an invention composition can be administered before, during, or after surgery (e.g., bypass surgery or angioplasty), stroke, or cardiac arrest.

Accordingly, a composition of the invention can be formulated into pharmaceutically acceptable carriers, diluents, or excipients for internal or external (e.g., topical) administration. Thus, pharmaceutical formulations including a composition having blood glucose-lowering or cholesterol-lowering activity are provided. In one embodiment, a pharmaceutical formulation includes a pill (tablet or capsule). In another embodiment, a pharmaceutical formulation includes a syrup or elixir or other liquid suitable for oral consumption. In yet another embodiment, a pharmaceutical formulation includes an ointment. In still another embodiment, a pharmaceutical formulation includes a formulation for application to the eye (e.g., eye drops). Topical formulations could increase glucose utilization at the site of application (i.e., locally) thereby ameliorating the condition.

Such pharmaceutical formulations including an invention composition can be administered alone, or in combination with other glucose-lowering or cholesterol-lowering drugs. Thus, the invention also provides pharmaceutical formulations, including an invention composition and one or more drugs having glucose-lowering or cholesterol-lowering activity, as well as methods of treatment using such composition combinations. Of course, the skilled artisan will recognize that any drug having glucose-lowering or cholesterol-lowering activity can be used in a therapeutic regimen (e.g., a method of the invention) in combination with an invention composition, even if the other drug is not present in the same pharmaceutical formulation as an invention composition.

The pharmaceutical compositions of the invention will be in a "pharmaceutically acceptable" or "physiologically acceptable" formulation. As used herein, the terms "pharmaceutically acceptable" and "physiologically acceptable" refer to carriers, diluents, excipients and the like that can be administered to a subject, preferably without producing excess adverse side effects (e.g., hypoglycemia, nausea, headaches, diarrhea, etc.). Such preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives may also be present such as, for example, antimicrobials, antioxidants, chelating agents, and inert gases and the like. Various pharmaceutical formulations appropriate for administration are known in the art and are applicable in the methods and compositions of the invention (e.g., *Remington's Pharmaceutical Sciences* (1990) 18th ed., Mack Publishing Co., Easton, Pa.; and *The Merck Index* (1996) 12th ed., Merck Publishing Group, Whitehouse, N.J.).

Prolonging the duration of action or controlled delivery of an administered composition can be achieved by incorporating the composition into particles or a polymeric substance such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. The rate of release of the composition can be controlled by altering the concentration or composition of such macromolecules. For example, it is possible to entrap the composition in microcapsules prepared by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

Thus, the compositions of the invention can be formulated in any pharmaceutically acceptable substance and administered in accordance with any protocol that achieves the desired effect. For example, a composition formulated into a capsule, pill, or elixir or syrup can be administered orally, once or more per day (e.g., at a low dose), or intermittently (e.g., every other day, once a week, etc. at a higher dose). The composition can be administered by other routes, including, for example, intravenous, intravascular, intraperitoneal, intramuscular, subcutaneous or intracavity. Thus, if a localized effect on the pancreas is desired, the composition can be formulated in Ringer's dextrose and injected into or near the pancreas (e.g., via the portal vein), for example.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example I

This example describes the preparation of a composition from Fenugreek seed having hypoglycemic or hypocholesterolemic activity without substantial if any glucose-increasing activity.

This example also describes several properties of the composition obtained from Fenugreek seeds.

Preparation of Water Extract:

Fenugreek seeds (100 gms) were extracted with 300 ml of distilled water overnight at 4° C. The next morning the water extract was decanted, centrifuged at 1000 rpm in the cold for 10 minutes and filtered. Purification is carried out at 4° C. to minimize loss in activity at room temperature. Soaking longer than 24 hours can result in reduction in activity. Removal of proteins by precipitation with ammonium sulphate saturation, separation of protein from supernatant and removal of ammonium sulfate gives a protein free active extract indicating that the active compound is not a protein. Protein precipitation is optional because this did not alter activity or purity of the compound after the chromatography step. Boiling in water destroys the composition.

DEAE Cellulose Chromatography:

DEAE cellulose was purified by washing with 0.1 N NaOH until there was no yellow color in wash. The DEAE cellulose was washed with distilled water to remove NaOH followed by 0.1 N HCl neutralization and several washings with distilled water to remove HCl (pH was that of the water). The purified DEAE cellulose was packed in a glass column (4×30 cm) and washed with distilled water at 4° C. The water extract of fenugreek seeds (50 ml) was loaded on the column. As the sample moved down the column bed, it was separated into two prominent bands: The uppermost band is dark brown in color and is hyperglycemic (increases blood glucose level) and the lower light yellow band is active (e.g., hypoglycemic). Below the light yellow band, the whole column is light yellowish in color and the compounds in this region do not appear to have significant blood glucose-lowering activity.

Batchwise or gradient elution with water and other buffers did not elute the active compound. In one method, the top brown layer was stirred with water and siphoned out without losing or disturbing the material below it. After removing the dark brown layer, the DEAE cellulose was carefully removed from the column by inverting it and gently tapping. The light yellow active band was cut out. In another method, the entire column is removed and the lower light yellow active band was cut out and processed further. The light yellow active band was extracted with 0.1 N HCl, centrifuged at 3,000 rpm for 15 minutes, and the supernatant neutralized with 0.1 N NaOH.

This partially purified preparation after lyophilization is referred to herein as Product 1.

Gel Filtration with Sephadex G 100:

Sephadex G100 of particle size 40-120μ was purified by overnight swelling in distilled water and de-aeration (under vacuum) by boiling in a water bath for 45 min. The thick slurry was packed in a glass column of 5×30 cm and equilibrated with water in a cold room. The DEAE purified fraction was carefully loaded on the top of the Sephadex column and the sample allowed to run down the column bed. It was eluted with water at a rate of about 0.5 ml. per minute and 10-ml fractions were collected and pooled into four fractions according to color. The second light yellow fraction, designated G II, had significant hypoglycemic activity.

Thin Layer Chromatography (TLC):

The fraction from step 3 was separated by thin layer chromatography on silica gel G (0.25 mm thick) plates (activated at 110° C. for 1 hour) using n-butanol: acetic acid: water (5:1:4 v/v) as solvent. A single spot with iodine vapors was visible, although occasionally, there were two spots in which the major spot was active. When two spots were present, the silica gel having the major band was scraped and extracted with 0.1 N HCl, centrifuged at 3000 rpm for 15 min and neutralized with 0.1 N NaOH. The yield of the TLC purified composition was very low.

Solubility:

It is freely soluble in water, acid, and alkali and insoluble in organic solvents. It is colorless in acidic (0.1N HCl) medium. It becomes yellow in color upon addition of alkali (0.1 N NaOH) but, on neutralization with acid, becomes colorless.

Stability:

The compound is stable in aqueous solution at 4° C. for about three weeks. When stored in a frozen state (−20° C.) it is stable for at least 2-3 months. Alkali treatment seems to decompose the group with peak at 340 nm. It is also stable in lyophilized form to a greater extent that in the aqueous form.

Absorption Spectra of Sephadex GII Fraction (Menthi GII):

The absorption spectrum of Sephadex GII fraction in the UV and visible region in acid and alkali were studied and the absorption maxima shown in Table 1. In 0.1 N HCl, the compound showed absorption maximum of 205, 268 and 340 nm. In alkali, the absorption maxima were at 211, 276, 390 and 402 nm.

Absorption Spectra of TLC Purified Fraction:

The absorption spectrum of TLC purified fraction, TII, and the maximum absorption values are shown in Table 1. In the acidic medium, the TLC purified fraction had three peaks as with GII. But, in the alkaline medium, there were two peaks at 211 and 270 nm as against four peaks at 211, 276, 390 and 402 nm seen with the Sephadex GII fraction. This indicates that the compound with peak at 340 nm in acid medium is unstable in alkaline medium. The two compounds with peaks at 390 and 402 nm seen with alkali in sephadex GII fraction are removed during purification by TLC. The infrared spectra is shown in Table 1.

Comparison of fenugreek GII absorption spectrum with trigonelline and nicotinic acid in the UV and visible region in acid and alkaline medium reveals that the fenugreek composition is different from trigonelline and nicotinic acid.

TABLE 1

SUMMARY OF SPECTRAL CHARACTERISTICS (ABSORPTION MAXIMA) OF MENTHI, TRIGONELLINE AND NICOTINIC ACID UV-Visible Region (Absorption Maxima nm)

|  | UV | Visible |
|---|---|---|
| Menthi GII |  |  |
| Acid | 205, 268 | 340 |
| Alkali | 211, 276 | 390, 402 |
| Menthi TII |  |  |
| Acid | 205, 270 | 340 |
| Alkali | 211, 270 |  |
| Trigonelline |  |  |
| Acid | 264 |  |
| Alkali | 215, 263 |  |
| Nicotinic acid |  |  |
| Acid | 260 |  |
| IR Spectrum 4600 cm$^{-1}$ to 400 cm$^{-1}$ region (inverted peaks, nm) |  |  |

Menthi GII:
2940.1, 2852.8, 2833.6, 2361.0, 1730.3, 1606.8, 1365.7, 1263.5, 1158.4, 804.37, 775.44, 669.35

The Active Compound:

Since the Sephadex GII and TLC II fractions are active, the compound(s) with peaks at 205, 270 and 340 nm in acid medium likely accounts for one or more of the biological activities. The compound(s) having peaks at 390 and 402 nm in alkali, present in Sephadex GII fraction (absent in TLC II fraction) are unlikely to be active and appear to be a contaminant(s) present in small amounts.

Example II

This example describes a comparison of physical characteristics between fenugreek composition, trigonellene, and nicotonic acid.

Structure of the Active Compound:

One alkaloid trigonelline and nicotinic acid were isolated from fenugreek seeds by others. Any similarity between the structures will be revealed by comparing the UV absorption spectra of the Menthi composition with trigonelline and nicotinic acid. A comparison of the UV and IR spectra of Menthi with trigonelline and nicotinic acid reveals that the two compounds are different, although there are some similarities between them.

The absorption spectrum of trigonelline in acid showed a single peak at 264 nm. In alkali, trigonelline showed two peaks at 263 and 275 nm. Nicotinic acid also showed a single peak at 259 nm in acid. The group with a peak at 340 nm seen with the purified fenugreek composition is absent in both trigonelline and nicotinic acid, which have groups with peaks below 264 nm. However, Menthi has peaks at 268 nm and above (Table 1). The infrared spectrum of trigonelline is different from that of Menthi.

Trigonelline is a derivative of nicotinic acid. Therefore, the fenugreek composition (Menthi) may be a derivative of nicotinic acid and related to but different from trigonelline. Reduced nicotinamide adenine dinucleotide (NADH), the coenzyme form of nicotinic acid has a maximum absorption of 340 nm. The fenugreek composition could be a nicotinic acid derivative and a nucleotide similar to but not identical to NADH, however; NADH is not known to have antidiabetic activity.

As disclosed herein, the fenugreek composition has hypocholesterolemic activity. It is also noted that compounds with hypocholesterolemic activity, which are structurally saponins, were reported in fenugreek seeds. Y. Sauvaire et al., *Lipids* 26 (3), 191-197 (1991). However, the fenugreek composition is distinct from saponins and sapogenins.

Absorption Maximum:

Menthi GII in acid, shows absorption maxima at 205, 268 and 340 nm. In alkali, shows absorption maxima at 211, 276, 370 and 402 nm. Menthi TII in acid, shows absorption maxima at 205, 270 and 340 nm. In alkali, shows absorption maxima at 211 and 270 nm.

Example III

This example describes animal studies demonstrating the in vivo glucose-lowering activity of the fenugreek composition.

The above TLC analysis indicates that the composition obtained after Sephadex gel filtration is primarily a single band. Thus, there is no additional advantage of purification by thin layer chromatography after Sephadex gel filtration, and, furthermore, the yield of TLC purified material is very poor. The studies were therefore carried out with Sephadex GII fraction, referred to as Menthi, Menthi GII or simply GII.

Induction of Diabetes:

Destruction of beta cells in islets of Langerhans in the pancreas of animals is the most commonly used method of inducing hyperglycemia (diabetes) in animals. Alloxan is used in rabbits. Overnight fasted rabbits (1 to 1.5 kg) were administered 80 mg/kg body weight (bw) alloxan solution intravenously (prepared in 0.7% sterile NaCl, pH adjusted to 4.5 with solid citric acid) through the marginal ear vein. If any of the rabbits showed signs of hypoglycemia (in 6-8 hours) due to sudden release of insulin, 25% glucose solution was given orally by gastric intubation. A rabbit pellet diet (Hindustan Levers, Bombay) was provided four hours after alloxan injection. Blood glucose was tested at intervals of 5 days. Urine was also tested for glucose by Qualitative Benedicts reagent by adding 8 drops of urine to 5 ml of the reagent, and boiling for 2 minutes. Orange to reddish precipitate indicates diabetes in the animals.

Usually after 30 days of alloxan injection, the animals reached a stabilized state of diabetes. Only rabbits with stabilized diabetic state were used for the studies. We produced three types of diabetic rabbits similar to sub-diabetic, diabetic, and severely diabetic states in humans. The rabbits were arbitrarily divided into three groups: (1) subdiabetic, (2) diabetic, and (3) severely diabetic rabbits.

Subdiabetic Rabbits:

In some of the rabbits, fasting blood or plasma glucose levels initially increased after alloxan injection, but decreased to normal or slightly elevated levels (up to 120 mg/dl). However, these rabbits showed decreased glucose tolerance; plasma glucose took much longer than the usual 2.5 hours time to return to normal after oral glucose load. This condition in rabbits is similar to the subdiabetic state in humans.

Diabetic Rabbits:

Rabbits with elevated fasting plasma glucose (FPG) or fasting blood glucose (FBG) levels in the range of 120-250 mg/dl were classified as diabetic. Glucose tolerance was abnormal in these animals, with plasma glucose values remaining much higher than normal even 2.5 hours after oral glucose load. This condition is similar to NIDDM in humans.

Severely Diabetic Rabbits:

Rabbits with FPG or FBG values above 250 mg/dl were considered to be severely diabetic. When a glucose tolerance test (GTT) was performed, most of the animals died. Thus, oral GTT was avoided in this group of rabbits. Severely diabetic rabbits with FPG values closer to 400 mg/dl are similar to human IDDM patients.

Diabetes can be induced in other animals by various methods. Of the various animals, diabetes induced in rabbits more closely mimics human diabetes. But, rats and mice also can be used. For example, diabetes can be induced in rats with streptozotocin using standard methods known in the art. Streptozotocin induced diabetes in rats resembles NIDDM of humans.

Blood Glucose Determination:

Plasma glucose was determined as a measure of blood glucose of the animals. Fasting blood glucose was determined once a week for one month with an enzymatic glucose oxidase/peroxidase kit of M/S Ranbaxy Diagnostics, New Delhi, or Stangen Immunodiagnostics, Hyderabad, India as described by the manufacturer. Blood was collected and plasma separated by centrifugation at 1000 rpm at room temperature for 10 minutes was analyzed for glucose. Hemolysed samples were rejected. The supernatant plasma was stored in the refrigerator until analysis, as early as possible after collection. Working solution of the kit (prepared) was mixed with 10 ml of water (for blank), standard glucose (provided in the kit) or plasma (for test) and incubated at 37° C. for 15 minutes. Intensity of red color was measured by absorbance at 505 nm. Plasma glucose was calculated from the optical density values of standard glucose (minus blank) and test sample (minus blank) using the formula given in the instructions of the manufacturer. Rabbits with consistently high fasting plasma glucose values of 150-200 mg/dl were used.

Glucose Tolerance Test:

Blood (2 ml) was collected in tubes containing suitable anticoagulant from overnight fasted diabetic rabbits. One group of rabbits was given a 50 mg/kg water solution of Menthi GII administered orally by Ryle's tube and the second group received the same volume of water without GII. After 90 minutes, 2 ml blood was again drawn. The plasma glucose of this sample indicates the glucose-lowering activity of Menthi GII just 90 minutes after administration. This blood sample, 90 minutes after administering GII, also serves as the zero hour sample in the glucose tolerance test. The rabbits were then given glucose (2 g/kg bw) in 15 ml water orally and blood samples collected after one and two hours and the glucose levels determined.

Glucose-Lowering Activity of the Fenugreek Composition:

Menthi GII fraction decreases plasma glucose in the zero hour (fasting), 1 hour, and 2 hour of animals when compared with the untreated animals (which received water only in place of Menthi GII). The decrease is greater in 1 hour and 2 hour plasma glucose values than in the zero hour samples. The average decrease in 1 hour and 2 hour plasma glucose produced by a single GII dose in these rabbits is typically greater than about 20%, or more of the untreated rabbit(s).

Hypoglycemic Activity of the Fenugreek Composition (Fasting Blood Glucose and Glucose Tolerance Test):

In subdiabetic and diabetic rabbits, after overnight fasting, blood was drawn in the morning from marginal ear vein. After 90 min, blood was again drawn and the glucose tolerance test was performed by giving glucose (2 g/kg) solution orally. Blood samples were again drawn 1 and 2.5 hours after glucose load and the Plasma glucose from each of the blood samples was determined.

In untreated subdiabetic and diabetic rabbits plasma glucose remains at higher than normal levels for a much longer time period than in normal rabbits. Since the plasma glucose levels are nearly normal or slightly elevated in subdiabetic rabbits, after treatment with an antidiabetic drug there may or may not be any detectable change in fasting plasma glucose (FPG). In fact, a decrease in FPG below normal (i.e., hypoglycemia) is also not desirable. Thus, improvement in glucose tolerance was used as a parameter for antidiabetic activity in subdiabetic rabbits.

In diabetic rabbits, which have elevated blood glucose levels, assessment of antidiabetic activity was detected by a decrease in FPG as well as an improvement in glucose tolerance. In severely diabetic rabbits, glucose tolerance test cannot be used because the animals might die after oral glucose load and, therefore, assessment was by detecting a decrease in FPG after treatment.

A Single Oral Dose of the Composition Improves Glucose Tolerance:

A single dose (50 mg/kg bw) did not produce a detectable decrease in fasting blood glucose in any of the three types of diabetes. However, in the glucose tolerance test, there was improvement in glucose tolerance with about 25-35% reduction in plasma glucose values 1 hour after oral glucose load. These results indicate that even a single 50 mg/kg dose can improve glucose tolerance in subdiabetic as well as in diabetic rabbits.

Long-Term Administration of the Fenugreek Compound Restores Fasting Blood Glucose and Glucose Tolerance to Normal in Diabetic Rabbits:

Fenugreek composition was administered orally once a day in the morning at a dose of 50 mg/kg bw for the duration indicated below. Hindustan Lever rabbit food and water were given ad libitum except when glucose tolerance test was performed or when fasting glucose was determined, in which case, food was withdrawn the previous night in order to produce overnight fasted rabbits.

Sub-Diabetic Rabbits:

Fasting plasma glucose: There was a 10% decrease in FPG, which continued to remain in the normal range after 12 days of treatment. This decrease was not surprising because in this type of rabbit FPG is normal or only slightly elevated. This result implies that the fenugreek composition has no adverse effect of lowering blood glucose to an undesirable level, such as causing coma, due to hypoglycemia.

Glucose tolerance: After 6 days of treatment, there was 32-35% decrease in plasma glucose in the glucose tolerance test. After 12 days of daily treatment, the glucose tolerance pattern was completely normal with a 50% reduction in 1 hour plasma glucose (Table 2).

Diabetic Rabbits:

In the diabetic rabbits, after 12 days of treatment, fasting plasma glucose returned to normal (90.1±4 md/dl) from the pre treatment level of 150.1±14 mg/dl. After 15 days of treatment, GTT returned to normal (Table 3).

Severely Diabetic Rabbits:

In severely diabetic rabbits with very high initial fasting plasma glucose of 427.8±46 mg/dl, there was a 50% reduction in FPG after one week's treatment. After four weeks treatment, FPG decreased to near normal (110.1±11 mg/dl), a decrease of 75% (Table 4). These severely diabetic rabbits resemble human IDDM patients in which fasting blood glucose levels are reduced to a level of about 120 mg/dl by insulin injection. The data in animals administered fenugreek composition, which produce good control of plasma glucose to levels below 150 mg/dl after only 15 days of oral treatment, indicate the potency of the composition. Also noteworthy is that glucose tolerance tests could be conducted in the treated severely diabetic rabbits, and the glucose tolerance curve for these treated animals was close to normal. This result contrasts with glucose tolerance test before fenugreek composition treatment, which usually resulted in death of the rabbits.

TABLE 2

ACTIVITY OF MENTHI GII ON FPG AND GTT IN SUBDIABETIC RABBITS
Plasma Glucose (mg/dl)

|  | Fasting | 1 Hour | 2.5 Hours |
|---|---|---|---|
| Normal Diabetic | 90.1 ± 2 | 148.2 ± 5 | 134.6 ± 4 |
| Day 0 | 96.6 ± 7 | 296.6 ± 38 | 270.7 ± 22 |
| Day 6 | 90.6 ± 5 | 200.5 ± 6 | 180.2 ± 19 |
| % Change | −6 | −32 | −33 |
| Day 12 | 86.6 ± 6 | 146.1 ± 11 | 138.2 ± 0 |
| % Change | −10 | −50 | −48 |

TABLE 3

STUDIES WITH FENUGREEK COMPOSITION MENTHI GII IN DIABETIC RABBITS UNTIL RESTORATION OF FPG AND GTT TO NORMAL (5 RABBITS)
Plasma Glucose (mg/dl)

|  | Fasting | 1 Hour | 2.5 Hours |
|---|---|---|---|
| Normal Diabetic | 90.1 ± 1.3 | 148.2 ± 5 | 134.6 ± 4 |
| Day 0 | 150.1 ± 14 | 286.6 ± 39 | 187.1 ± 13 |
| Day 6 | 100.0 ± 6 | 183.7 ± 16 | 150.0 ± 14 |
| % Change | −33 | −36 | −19 |
| Day 12 | 90.1 ± 4 | 177.3 ± 20 | 152.6 ± 10 |
| % Change | −40 | −38 | −14 |
| Day 15 | 89.5 ± 5 | 148.6 ± 12 | 110.1 ± 8 |
| % Change | −40 | −48 | −41 |

TABLE 4

STUDIES WITH FENUGREEK COMPOSITION MENTHI GII IN SEVERELY DIABETIC RABBITS UNTIL RESTORATION OF FPG TO NORMAL (5 RABBITS)
Plasma Glucose mg/dl

|  | Fasting | % Change |
|---|---|---|
| Day 0 | 427.8 ± 46 |  |
| Day 7 | 205.9 ± 20 | −51.8 |
| Day 15 | 143.7 ± 14 | −66.4 |
| Day 21 | 128.3 ± 10 | −69.9 |
| Day 28 | 110.1 ± 11 | −74.1 |

The data in Table 4 show that in a severe diabetic condition in which insulin injection is the only treatment, this fenugreek composition controlled glucose in 2 weeks and reduced fasting blood glucose to nearly normal in 4 weeks. These results demonstrate that the fenugreek composition, in itself, is very potent at a small dose of 50 mg/kg in controlling not only diabetes but severe diabetes. Thus, an advantage of the fenugreek composition is that oral treatment can be given from the beginning without the need to administer insulin initially.

Intermittent Therapy:

One method in which to minimize the possibility of drug side effects is to administer the drug as infrequently as possible while still achieving the desired biological effect. Intermittent therapy of once a week Menthi administration was studied in subdiabetic and diabetic rabbits, and the effect on glucose tolerance is shown in Table 5. In both subdiabetic and diabetic rabbits there was a decrease in 2.5 hours plasma glucose by the end of the first week. Subsequently, there was an additional progressive improvement in glucose tolerance of both groups of animals; GTT returned to normal by about five weeks. FPG returned to normal by three weeks in diabetic rabbits.

These results demonstrate that: (1) effective control of subdiabetes and diabetes can be achieved by once a week Menthi GII administration, and (2) a single dose of Menthi GII has a prolonged duration of action of nearly one week because there was no increase of plasma glucose between the weekly doses.

Example IV

This example describes studies comparing the activity of Menthi from fenugreek seed to trigonelline, tolbutamide and saponins.

Comparison of the Antidiabetic Activity of Menthi and Trigonelline with Tolbutamide:

The antidiabetic activity of GII (Menthi) and the alkaloid trigonelline, which can be isolated from fenugreek seeds, were compared. Diabetic rabbits were administered the same dose (100 mg/kg/day) daily for 3 days. The activity of these two was also compared with a standard drug tolbutamide all at the same dosage schedule of 100 mg/Kg/day for 3 days. The improvement in glucose tolerance, i.e., percent decrease in blood glucose at 2.5 hours in glucose tolerance test (after oral glucose load) in diabetic rabbits is shown in Table 6.

TABLE 5

EFFECT OF WEEKLY ADMINISTRATION OF MENTHI GII ON GTT IN SUBDIABETIC AND DIABETIC RABBITS

| Treatment | Plasma Glucose (mg/dl) | | | |
|---|---|---|---|---|
| | Subdiabetic | | Diabetic | |
| Duration | Fasting | 2.5 Hours | Fasting | 2.5 Hours |
| 0 Week (Basal) | 96.0 ± 2 | 292.2 ± 40 | 133.0 ± 12 | 330.2 ± 32 |
| 1 Week | 99.6 ± 1 | 170.2 ± 14 | 113.5 ± 16 | 197.5 ± 19 |
| 2 Week | 96.7 ± 3 | 160.7 ± 13 | 106.6 ± 3 | 150.0 ± 13 |
| 3 Week | 90.1 ± 4 | 140.3 ± 11 | 95.4 ± 7 | 156.5 ± 14 |
| 4 Week | 90.2 ± 4 | 146.5 ± 15 | 93.6 ± 2 | 133.3 ± 10 |
| 5 Week | 86.8 ± 4 | 138.7 ± 9 | 90.8 ± 5 | 133.3 ± 11 |
| 6 Week | 90.6 ± 4 | 122.7 ± 13 | 96.6 ± 7 | 130.4 ± 11 |

TABLE 6

EFFECT OF MENTHI GII TRIGONELLINE AND TOLBUTAMIDE ON THE GLUCOSE TOLERANCE IN DIABETIC RABBITS (100 mg/kg/DAY) FOR 3 DAYS

| Compound | % Decrease in Blood Glucose Level at 2.5 Hours in GTT |
|---|---|
| Menthi | 36 |
| Tolbutamide | 25 |
| Trigonelline | 16 |

The results show that the alkaloid trigonelline was less potent than Menthi in the diabetic rabbits; the percent decrease in blood glucose produced by trigonelline was only half of that produced by Menthi (GII). These results are consistent with the findings of Mishinsky (J. Shani (Mishinsky) et al., Lancet, 16, 1311-1312 (1967), who isolated trigonelline from fenugreek seeds and reported that it has only mild and transient hypoglycemic activity. This indicates that Menthi is different from and more potent than trigonelline.

Menthi also has greater activity than the standard drug tolbutamide. It is noted that tolbutamide requires a functional pancreas for its activity and is useful only in mild diabetes, but not in severe diabetes. In contrast, Menthi from fenugreek seed is effective in treating severely diabetic animals.

Menthi is Distinct from Saponins of Fenugreek Seed:

A steroidal sapogenin referred to as fenugreekine was isolated from fenugreek seeds by S. Ghosal et al., Phytochemistry 13 (10), 2247 (1974). Studies of the antidiabetic activity of this compound as described by S. Ghosal et al., revealed that it could not lower blood glucose during GTT in diabetic rabbits. Thus, Menthi is distinct from the steroidal saponins and sapogenins isolated by many workers (Y. Sauvaire et al., Lipids 26 (3), 191-197 (1991); J. Shani (Mishinsky) et al., Lancet 16, 1311-1312 (1967)), as well as apparently being more potent.

Example V

This example describes studies showing that Menthi decreases glycosylated hemoglobin in diabetic animals.

In diabetic rabbits, glycosylated hemoglobin HbA1 remains elevated above the normal range. The level of HbA1 is considered a reliable index of control of the diabetic state because it reflects long term blood glucose levels over approximately 3 months. In diabetic rabbits, glycosylated HbA1 increased slightly to the upper limit of normal range; FPG was 150.4±14 mg/dl and HbA1 3.9±0.3% (Tables 7 and 8). This increase was reversed by treatment with fenugreek composition (Month 50 mg/kg/day) for four weeks; both FPG and HbA1 decreased to normal, 90.5±5 mg/dl and 2.6±0.2%, respectively.

In severely diabetic rabbits before treatment, the FPG was 427.8±46 mg/dl and Hb A1 4.5±0.4%. After four weeks treatment, both FPG and HbA1 decreased to near normal levels, 110±11 mg/dl and 3.1±0.3%, respectively (Table 8).

TABLE 7

EFFECT OF MENTHI TREATMENT FOR 4 WEEKS ON GLYCOSYLATED HEMOGLOBIN LEVELS IN DIABETIC RABBITS

| | FPG mg/dl | HbA1 % |
|---|---|---|
| Diabetic untreated | 150.4 ± 14 | 3.9 ± 0.3 |
| Treated 4 weeks | 90.5 ± 5 | 2.6 ± 0.2 |

TABLE 7-continued

EFFECT OF MENTHI TREATMENT FOR 4 WEEKS ON
GLYCOSYLATED HEMOGLOBIN LEVELS IN DIABETIC RABBITS

|  | FPG mg/dl | HbA1 % |
|---|---|---|
| Severely diabetic untreated | 427.8 ± 46 | 4.8 ± 0.5 |
| Treated 4 weeks | 110 ± 11 | 3.1 ± 0.3 |

TABLE 8

EFFECT OF MENTHI ON GLYCOSYLATED HEMOGLOBIN

|  |  | FPG mg/dl |  | HbA1% |  |
|---|---|---|---|---|---|
| Treatment |  | Diabetic | Severely Diabetic | Diabetic | Severely Diabetic |
| Untreated |  |  |  |  |  |
| Menthi (group) |  | 150.4 ± 14 | 427.8 ± 46 | 3.9 ± 0.3 | 4.8 ± 0.5 |
| Control |  | 161.2 ± 14 | 433.2 ± 40 | 3.6 ± 0.3 | 4.8 ± 0.5 |
| Treated |  |  |  |  |  |
| 1 Week | Menthi | 100.1 ± 6 | 205.9 ± 20 | 3.6 ± 0.3 | 4.8 ± 0.4 |
|  | Control | 152.3 ± 13 | 507.8 ± 45 | 3.4 ± 0.3 | 4.9 ± 0.5 |
| 2 Weeks | Menthi | 89.5 ± 5 | 143.7 ± 14 | 3.0 ± 0.2 | 4.9 ± 0.4 |
|  | Control | 173.6 ± 14 | 534.2 ± 48 | 3.6 ± 0.3 | 5.0 ± 0.6 |
| 3 Weeks | Menthi | 89.1 ± 5 | 128.3 ± 4 | 2.9 ± 0.2 | 4.4 ± 0.4 |
|  | Control | 194.2 ± 15 | 501 ± 40 | 3.5 ± 0.3 | 5.2 ± 0.5 |
| 4 Weeks | Menthi | 90.5 ± 5 | 110.1 ± 11 | 2.6 ± 0.2 | 3.1 ± 0.3 |
|  | Control | 188.2 ± 13 | 548.6 ± 46 | 3.7 ± 0.3 | 5.2 ± 0.5 |

Fenugreek Composition does not Produce Hypoglycemia:

An additional conclusion based on the data in Table 8 is that in the diabetic rabbits, continuation of treatment up to 4 weeks did not produce hypoglycemia, even though FPG decreases to normal by 2 weeks. These results therefore indicate that the fenugreek composition reduces glucose levels without producing hypoglycemia.

Example VI

This example describes studies showing that fenugreek composition improves carbohydrate and lipid metabolism in several tissues.

Carbohydrate Metabolism: Liver and Muscle Glycogen

Diabetes:

In diabetes, liver and muscle glycogen are depleted to provide glucose to the body. Normal glycogen content of rabbit liver was 27.1±3 mg/gm liver and, in diabetes, it decreased to 9.1±2 mg/gm. After Menthi treatment (50 mg/kg/day) for 15 days, liver glycogen increased to the normal, 28.0±4 mg/gm. Similarly, in muscle, normal glycogen content was 14.0±3 mg/gm and, in diabetic rabbits, it decreased to 6.8±1 mg/gm. After treatment for 15 days, muscle glycogen increased to 11.1±1 mg/gm.

Severe Diabetes:

In severe diabetes, liver and muscle glycogen decreased to 9.6±1 and 5.1±1 mg/gm tissue respectively. After Menthi treatment for 30 days, glycogen increased to normal, 22.1±4 and 12.9±1 mg/gm tissue, respectively. The data demonstrate that treatment with Menthi restored glycogen content of both liver and muscle in diabetic as well as in severely diabetic rabbits.

Body Weight:

As shown in Table 9, body weight, which decreased in diabetes, returned to normal in diabetes in 15 days and in severe diabetes in 30 days.

TABLE 9

BODY WEIGHT OF NORMAL, DIABETIC, AND SEVERELY
DIABETIC RABBITS BEFORE AND AFTER TREATMENT WITH
MENTHI FOR 15 AND 30 DAYS, RESPECTIVELY

|  | Body Weight (kg) | |
|---|---|---|
| Condition | Diabetic (15 days) | Severely Diabetic (30 days) |
| Before diabetes (Normal) | 1.01 ± 0.1 | 1.02 ± 0.08 |
| Untreated Diabetic | 0.88 ± 0.06 | 0.76 ± 0.06 |
| Treated (Menthi) | 1.14 ± 0.1 | 0.96 ± 0.07 |

TABLE 10

EFFECT OF MENTHI ON GLUCOSE-INDUCED SERUM INSULIN
LEVELS BEFORE AND AFTER 15 DAYS OF TREATMENT
IN DIABETIC RABBITS

|  | Fasting | 1 Hour | 2 Hours |
|---|---|---|---|
| Serum Insulin (µU/ml) | | | |
| Controls (Healthy) | 11.6 ± 1.6 | 30.4 ± 2 | 28.1 ± 2 |
| Diabetic | | | |
| Day 0 | 3.04 ± 0.5 | 4.02 ± 0.5 | 3.8 ± 0.4 |
| Day 15 | 8.9 ± 1.6 | 19.3 ± 2 | 16.3 ± 2 |
| Blood Glucose (mg/dl) | | | |
| Controls (Healthy) | 90 ± 5.9 | 148 ± 10.1 | 122 ± 8.3 |
| Day 0 | 150 ± 11.7 | 246 ± 19.4 | 198 ± 14.3 |
| Day 15 | 89 ± 9.8 | 140 ± 11.6 | 110 ± 10.2 |

Example VI

This example describes studies showing that the fenugreek composition increases insulin levels in animals.

Antidiabetic or hypoglycemic drugs can function by more than one mechanism. One mechanism is pancreatic (beta-cryotropic) action, which stimulates the release or synthesis of insulin. Insulin, in turn, stimulates pathways of glucose utilization thereby reducing blood glucose. This mechanism is possible only if the pancreas, at least in part, is functional. The second mechanism is by the direct action of the drugs on the tissues to stimulate pathways of glucose utilization. This mechanism is referred to as extra pancreatic effect or peripheral action. Sulphonylurea type drugs act mostly by the first mechanism, although several of them stimulate glucose utilization directly.

In diabetic rabbits, insulin levels in fasting blood and in the blood samples 1 hour and 2 hours after oral glucose load during GTT were determined before and after 15 days treatment. Insulin levels were determined using Boehringer Mannheim (Germany) kits by an ELISA method.

The results shown in Table 10 indicate that insulin secretion, both in fasting condition and 1 hour and 2 hours after oral glucose load, was considerably reduced in diabetic rabbits in comparison to non-diabetic control animals. However, treatment with Menthi for 15 days increased serum insulin not only in fasting state but also after oral glucose load. These results indicate that continuing treatment will continue to increase insulin levels to normal levels because blood glucose levels were normal. These results indicate that one mechanism by which the fenugreek compositions function is pancreatic, i.e., by increasing serum insulin levels.

In severely diabetic rabbits, GTT could not be performed because of the possibility of death. Therefore, the effect of Menthi treatment was studied on fasting serum insulin levels. The results in Table 11 show that in severely diabetic rabbits serum insulin was very low. Treatment with Menthi for 30 days increased serum insulin by approximately 15%. This increase may be due to regeneration of pancreas which causes insulin producing or secreting function. Treatment for longer periods of time may further increase serum insulin levels. Fasting blood glucose in severely diabetic rabbits decreased to nearly normal, 110±11 mg/dl, from a very high 427±46 mg/dl. This data shows that the activity of Menthi in severely diabetic rabbits was due, in part, to increasing serum insulin levels, but was primarily due to an extra pancreatic effect. Therefore, Menthi possess the advantage of having both pancreatic (in diabetic) and extra pancreatic (in severely diabetic) activity.

TABLE 11

EFFECT OF 30 DAYS ADMINISTRATION OF MENTHI
ON FASTING INSULIN LEVEL IN SEVERELY DIABETIC RABBITS

|  | Day 1 | Day 15 | Day 30 |
| --- | --- | --- | --- |
| FBG mg/dl | 427 ± 46 | 143 ± 14 | 110 ± 11 |
| Fasting insulin (μU/ml) | 0.10 ± 0.03 | 0.090 ± 0.03 | 0.115 ± 0.03 |

Enzymes for Glucose Utilization:

In diabetic and severely diabetic rabbits, hexokinase, glucokinase (in liver) and pyruvate kinase were decreased considerably. Treatment of diabetic rabbits with Menthi (50 mg/kg/day) for 15 days and severely diabetic rabbits for 30 days restored the activities of these enzymes to nearly normal, except muscle hexokinase, which showed a slightly less improvement (Table 12). Malic enzyme, which is involved in lipogenesis, was reduced in diabetic and severely diabetic animals but after treatment was restored to nearly normal in liver. There was no detectable change in kidney malic enzyme after 15 days treatment, although a longer treatment period may produce an improvement. Glucose-6-phosphate dehydrogenase, one of the key enzymes of the HMP pathway, was also reduced in diabetes and severe diabetes in the liver of rabbits. After Menthi treatment for 15 days, there was a partial restoration of the activities indicating that longer treatment will likely completely restore activity to normal levels.

Enzymes of Gluconeogenesis and Polyol Pathway:

In diabetes and severe diabetes, the activity of the key enzyme glucose-6 phosphatase increased. After Menthi treatment there was a considerable decrease (Table 13). Treatment for a longer time period may completely restore the activity of this enzyme to normal.

Two enzymes of polyol pathway, sorbitol dehydrogenase and aldose reductase, which were elevated both in diabetes and severe diabetes returned to almost normal levels. The improvement was more apparent in the kidney. This finding is important because kidney and the polyol pathway are insensitive to insulin and the products of the polyol pathway are

TABLE 12

EFFECT OF MENTHI TREATMENT FOR 15 DAYS IN DIABETIC AND 30
DAYS IN SEVERELY DIABETIC RABBITS ON ENZYMES OF GLYCOLYSIS
AND MALIC ENZYME

|  |  | Diabetes | | | |
| --- | --- | --- | --- | --- | --- |
|  |  | Diabetic | | Severely Diabetic | |
|  | Normal | Untreated | Treated | Untreated | Treated |
| Liver |  |  |  |  |  |
| Hexokinase (u/gm) | 0.7 ± 0.05 | 0.46 ± 0.05 | 0.64 ± 0.04(39%) | 0.47 ± 0.03 | 0.66 ± 0.05(39%) |
| Glucokinase (u/gm) | 1.7 ± 0.07 | 0.32 ± 0.03 | 1.68 ± 0.07(425%) | 0.35 ± 0.03 | 1.70 ± 0.08(385%) |
| Glucose-6-phosphate Dehydrogenase (u/gm) | 141.4 ± 11 | 79.6 ± 6 | 116.5 ± 9(46%) | 83.3 ± 6 | 99.7 ± 8(19%) |
| Pyruvate Kinase (u/gm) | 25.9 ± 2 | 19.4 ± 1 | 26.2 ± 2(35%) | 17.1 ± 0.8 | 23.8 ± 0.61(39%) |
| Malic enzyme (u/gm) | 1.10 ± 0.07 | 0.59 ± 0.04 | 1.09 ± 0.08(85%) | 0.5 ± 0.04 | 1.01 ± 0.10(74%) |
| Muscle |  |  |  |  |  |
| Hexokinase (u/gm) | 2.7 ± 0.2 | 1.12 ± 0.12 | 1.54 ± 0.13(38%) | 1.01 ± 0.09 | 1.39 ± 0.13(38%) |
| Pyruvate Kinase | 28.9 ± 2 | 18.3 ± 1 | 28.1 ± 2(54%) | 21.9 ± 0.8 | 29.1 ± 1(33%) |
| Kidneys |  |  |  |  |  |
| Hexokinase (u/gm) | 0.90 ± 0.06 | 0.90 ± 0.04 | 1.0 ± 04(10%) | 0.77 ± 0.03 | 1.02 ± 0.06(32%) |
| Pruvate Kinase (u/gm) | 12.2 ± 0.6 | 12.2 ± 0.8 | 12.3 ± 0.7(0.3%) | 10.0 ± 0.6 | 12.4 ± 0.5(17%) |
| Malic enzyme (u/gm) | 1.62 ± 0.1 | 1.04 ± 0.07 | 0.99 ± 0.08(−5%) | 1.01 ± 0.08 | 1.07 ± 0.08 (6%) |

(Values in brackets indicate percent change)

Example VII

This example describes studies showing the effect of the fenugreek composition on enzymes of a number of pathways and cellular constituents in various tissues. This example also describes data indicating that treatment with the fenugreek composition reverses abnormal metabolic changes associated with hyperglycemia.

believed to be responsible for the damage to kidney membrane and cataract formation in hyperglycemic patients. Therefore the almost complete return of sorbitol dehydrogenase and aldose reductase to normal levels, even in severe diabetes, indicates that the composition is useful in ameliorating many of the complications associated with diabetes, including complications that are not ameliorated by insulin treatment.

Menthi GII Treatment Restores the Activity of the Enzymes of Antioxidant System:

The level of superoxide dismutase and glutathione peroxidase in liver and kidney of diabetic rabbits, with and without treatment by Menthi GII, was determined. There was a considerable decrease in the activities of superoxide dismutase and glutathione peroxidase in diabetic animals. After 15 days treatment, the activities of these two enzymes were nearly normal indicating that Menthi treatment restored the antioxidant status of the diabetic rabbits (Table 14). Although no detectable change in glutathione peroxidase activity was detected, a longer treatment period likely restores some activity.

Example VIII

This example describes toxicity data in liver and kidney demonstrating that Menthi GII treatment does not have any side effects.

In severely diabetic rabbits treated with Menthi for 30 days, the liver and kidney function tests were all within a normal range (Table 15). This indicates that the fenugreek product did not have any adverse side effects.

TABLE 15

EFFECT OF MENTHI GII ON LIVER AND KIDNEY FUNCTION TESTS IN SEVERELY DIABETIC RABBITS (n = 4)

|  |  | Day 1 | Day 30 | % Change |
|---|---|---|---|---|
| S. Bilirubin (mg %) | Test | 0.93 ± 0.06 | 0.76 ± 0.05 | −18 |
|  | Control | 0.84 ± 0.05 | 0.71 ± 0.06 | −15 |
| Alkaline Phosphatase | Test | 6.6 ± 0.5 | 6.0 ± 0.4 | −9 |
| (KAU/100 ml) | Control | 5.9 ± 0.4 | 6.1 ± 0.4 | +3 |
| SGPT (Karmen Units) | Test | 38 ± 3 | 46 ± 3 | +21 |
|  | Control | 32 ± 3 | 44 ± 4 | 38 |
| S. Creatinine (mg %) | Test | 2.3 ± 0.2 | 1.9 ± 0.1 | −17 |
|  | Control | 2.1 ± 0.1 | 2.2 ± 0.2 | +4 |
| S. Protein (mg %) | Test | 5.9 ± 0.3 | 6.3 ± 0.4 | +7 |
|  | Control | 5.5 ± 0.4 | 6.0 ± 0.4 | +9 |
| S. Urea (mg %) | Test | 39.1 ± 3 | 38.7 ± 4 | −1 |
|  | Control | 36.9 ± 4 | 44.4 ± 3 | +22 |

TABLE 13

EFFECT OF MENTHI TREATMENT ON GLUCOSE-6-PHOSPHATASE, ALDOSE REDUCTASE AND SORBITOL DEHYDROGENASE

| Enzyme | Normal | Diabetes | | | |
|---|---|---|---|---|---|
|  |  | Diabetic | | Severely Diabetic | |
|  |  | Untreated | Treated (15 days) | Untreated | Treated (30 days) |
| Liver |  |  |  |  |  |
| Glucose-6 phosphatase (u/gm) | 38.3 ± 3 | 70.1 ± 4 | 58.1 ± 4(17%) | 66.6 ± 4 | 59.4 ± 2(5)% |
| Sorbitol dehydrogenase (u/gm) | 9.4 ± 0.6 | 9.9 ± 0.8 | 9.3 ± 0.5(6%) | 10.7 ± 0.7 | 9.8 ± 0.6(7%) |
| Aldose reductase (u/gm) | 0.29 ± 0.05 | 0.33 ± 0.04 | 0.27 ± 0.03(18%) | 0.33 ± 0.05 | 0.26 ± 0.03(19%) |
| Kidney |  |  |  |  |  |
| Sorbitol dehydrogenase (u/gm) | 6.6 ± 0.5 | 8.0 ± 0.6 | 6.8 ± 0.5(15%) | 8.6 ± 0.8 | 6.5 ± 0.6(24%) |
| Aldose reductase (u/gm) | 0.21 ± 0.4 | 0.27 ± 0.06 | 0.22 ± 0.08(15%) | 0.30 ± 0.08 | 0.21 ± 0.5(30%) |

(Values in brackets indicate percent change)

TABLE 14

EFFECT OF MENTHI TREATMENT ON THE ACTIVITY OF GLUTATHIONE PEROXIDASE AND SUPEROXIDE DISMUTASE

|  | Normal | Diabetes | | | |
|---|---|---|---|---|---|
|  |  | Diabetic | | Severely Diabetic | |
|  |  | Untreated | Treated | Untreated | Treated (30 days) |
| Liver |  |  |  |  |  |
| Glutathione peroxidase (u/gm) | 23.1 ± 2 | 16.6 ± 1 | 21.7 ± 2 (33%) | 16.2 ± 1 | 23.0 ± 2 (42%) |
| Superoxide dismutase (u/gm) | 236.4 ± 22 | 185.2 ± 14 | 221.9 ± 15 (21%) | 172.7 ± 17 | 218 ± 16 (27%) |
| Kidney |  |  |  |  |  |
| Glutathione peroxidase (u/gm) | 6.3 ± 0.5 | 6.5 ± 0.5 | 6.6 ± 0.4 (1%) | 10.2 ± 1 | 7.6 ± 0.7 (25%) |
| Superoxide dismutase (u/gm) | 123.2 ± 2 | 137.7 ± 19 | 126.4 ± 17 (8%) | 137.4 ± 18 | 130.4 ± 16 (5%) |

(Values in brackets indicate percent change)

Example IX

This example describes the reversal of tissue histopathological changes associated with hyperglycemia after treatment with fenugreek composition.

Figure 2:
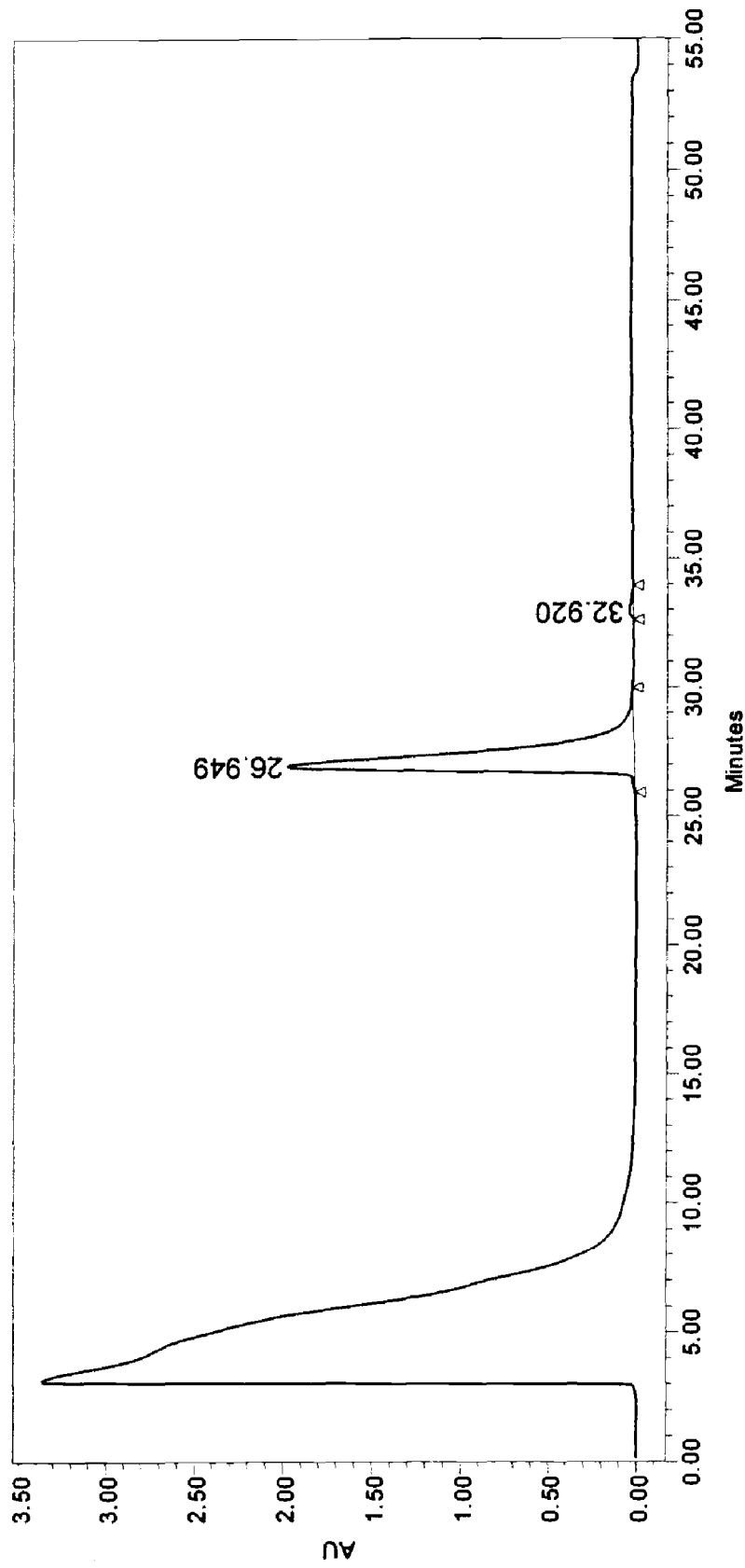
FIG. 2 is a photomicrograph of liver of an untreated severely diabetic rabbit in the periportal area showing fatty changes.
Figure 3:
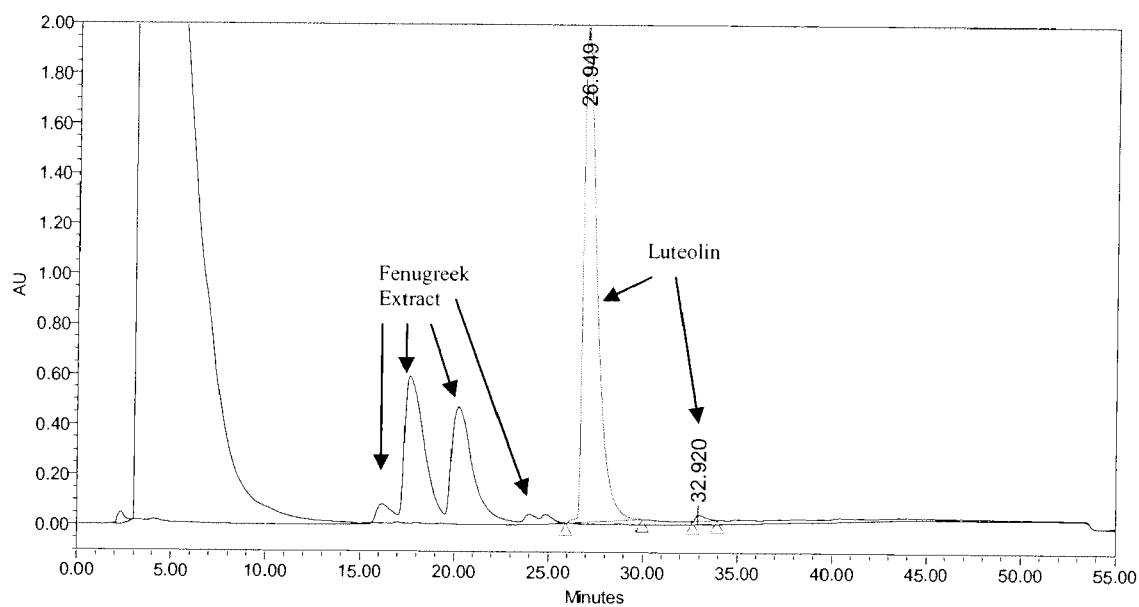
FIG. 3 is a photomicrograph of liver from a severely diabetic rabbit after treatment, which appears normal.

Fatty changes of varying degrees, moderate to severe, were observed in the liver tissue of severely diabetic rabbits. For example, there was fat infiltration and fatty cyst formation, more pronounced in the periportal area. Microscopic examination of parenchymal cell nuclei revealed a vesicular appearance with prominent basophilic nucleoli (FIGS. 1 and 2). After Menthi administration (50 mg/kg/day) to severely diabetic rabbits for one month, the above changes showed remarkable improvement and the hepatic tissue appeared histologically normal (FIG. 3).

Figure 4:
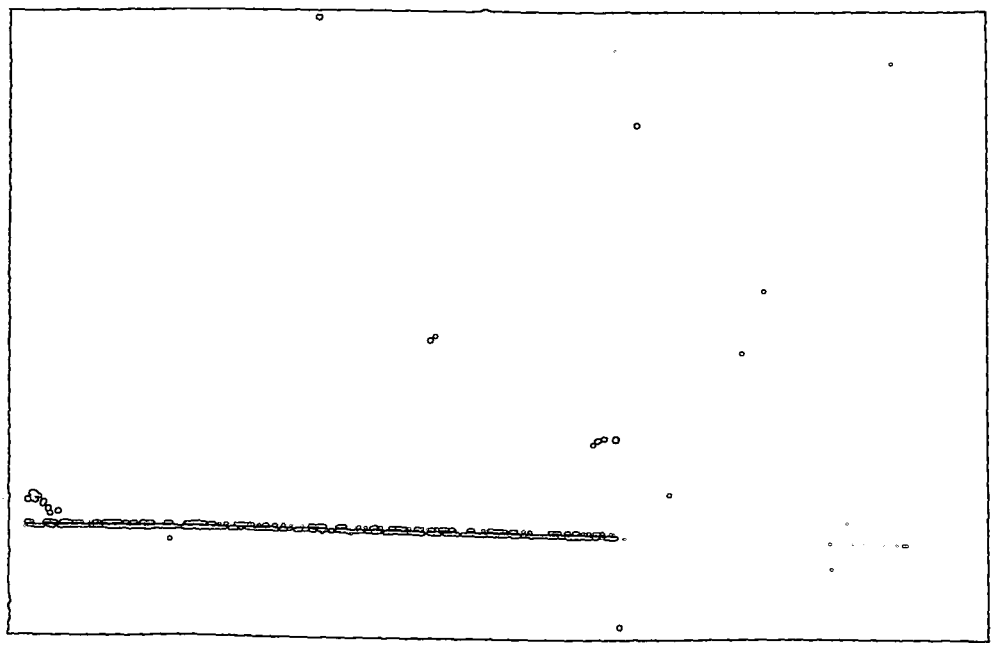
FIG. 4 is a photomicrograph of liver parenchymal cells in an untreated diabetic rabbit showing chromatin pushed towards one side of the cells.
Figure 5:
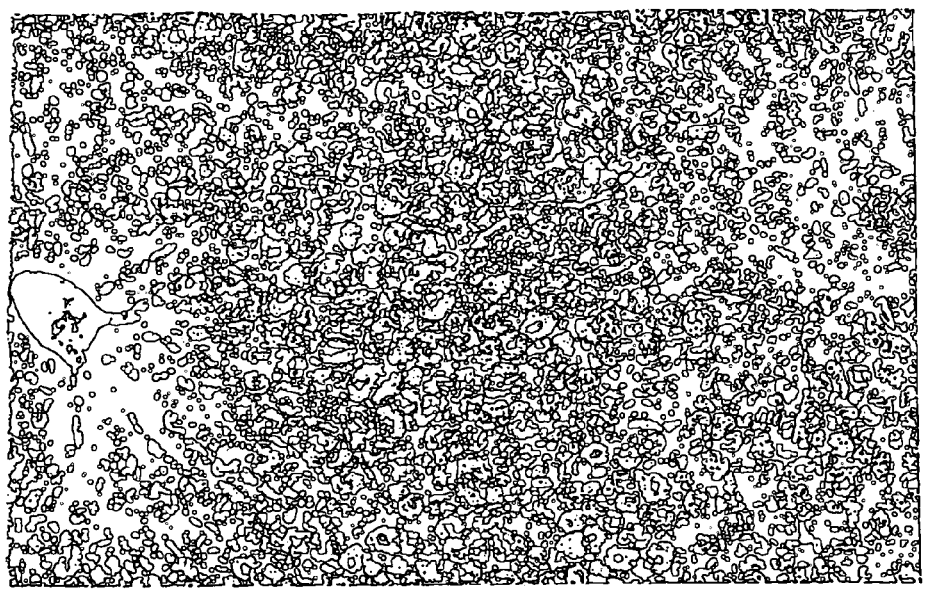
FIG. 5 is a photomicrograph of histologically normal liver of a diabetic rabbit after 30 days treatment.

In subdiabetic and diabetic rabbits, no changes were observed. In a few diabetic animals, vacuolated hepatic parenchymal cells were present and the chromatin was pushed towards one side of the cell (FIG. 4). With administration of Menthi GII fraction for 30 days, these changes were reversed (FIG. 5).

Figure 6:
FIG. 6 is a photomicrograph of the myocardium of an untreated severely diabetic rabbit showing fatty infiltration.

A few severely diabetic rabbits exhibited fatty infiltration of the myocardium (FIG. 6), which disappeared in the treated group. There were no significant changes observed in the heart in the other diabetic animals.

Figure 7:
FIG. 7 is a photomicrograph of pancreatic tissue of an untreated severely diabetic rabbit showing fatty infiltration.
Figure 8:
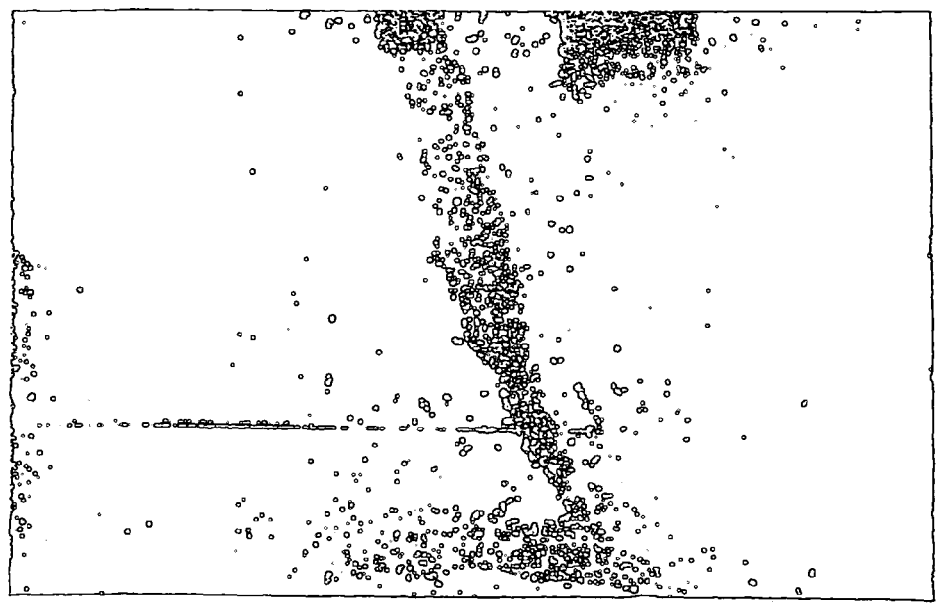
FIG. 8 is a photomicrograph of histologically normal pancreatic tissue of a severely diabetic rabbit after 30 days treatment.

Histopathological examination of pancreas of the severely diabetic rabbits before treatment revealed heavy fatty infiltration in the exocrine portion of the tissue and the islet cells could not be seen. In the treated group, fatty infiltration disappeared and the islet cells became clearly visible in a microsection of pancreas (FIGS. 7 and 8). This finding is consistent with earlier results that there was a 74% improvement in the FPG in the treated SD rabbits and there was improved insulin response by the beta cells.

Figure 9:
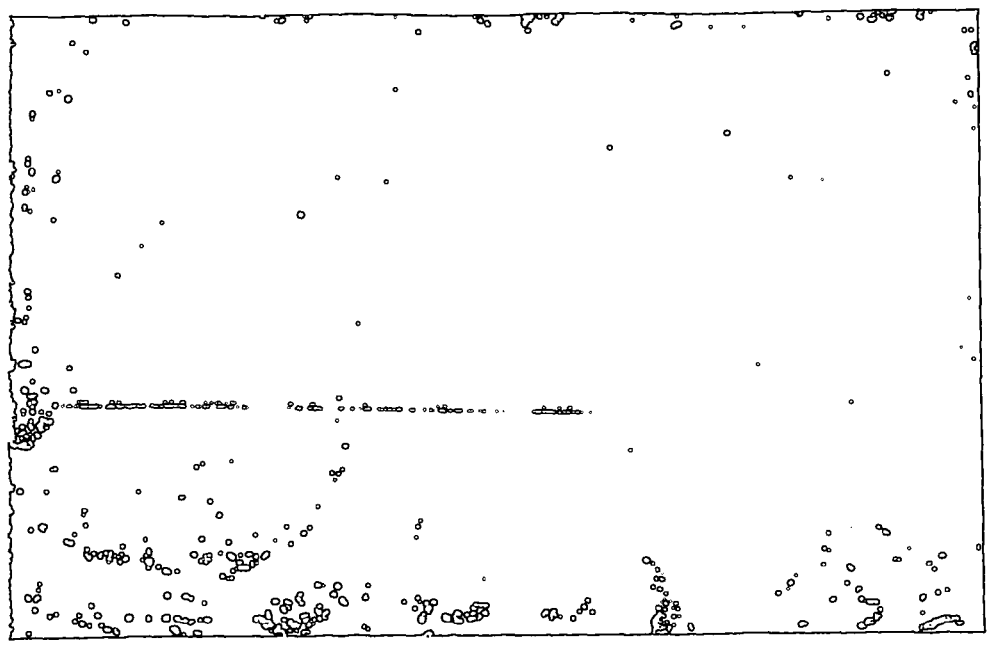
FIG. 9 is a photomicrograph of vacuolized cells in renal tubules and hyalinized material in glomeruli of kidney in a severely diabetic rabbit.
Figure 10:
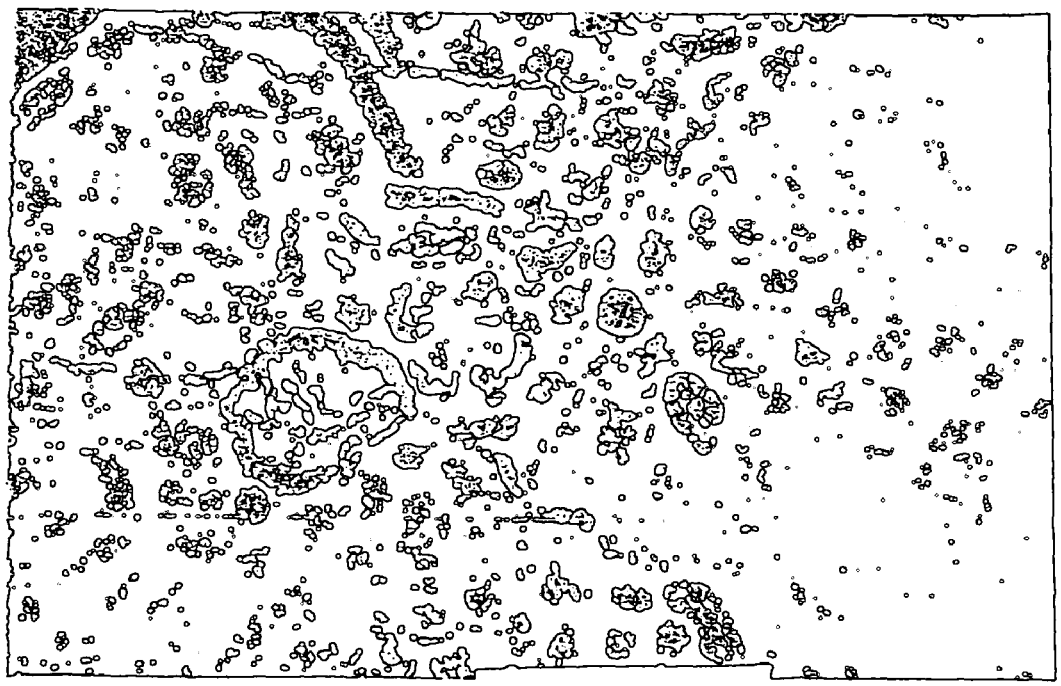
FIG. 10 is a photomicrograph of kidney of an untreated severely diabetic rabbit showing calcification in and around renal tubules.
Figure 11:
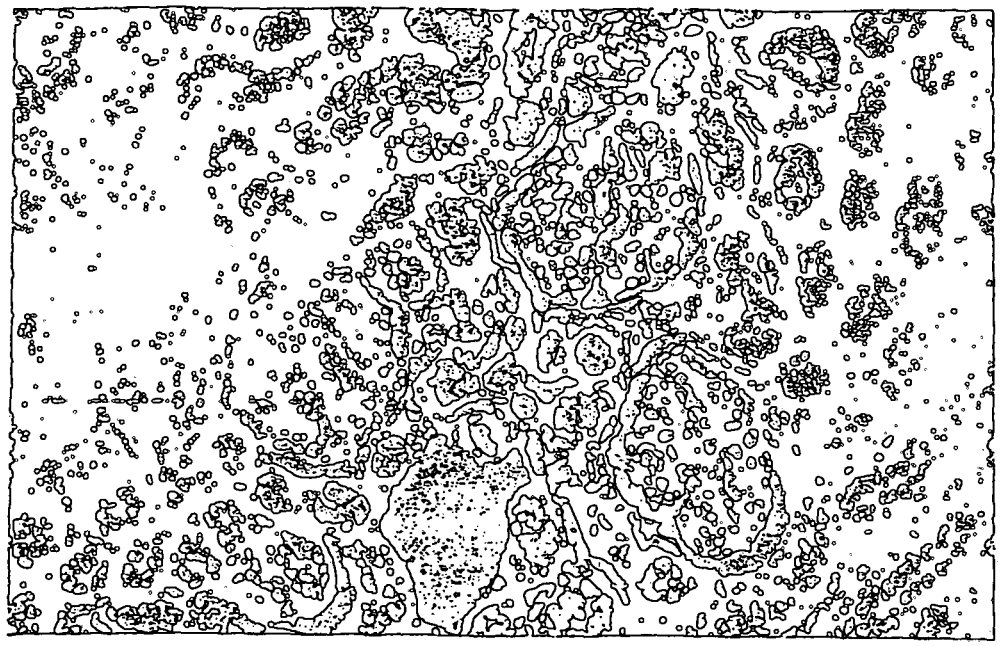
FIG. 11 is a photomicrograph of histologically normal kidney of a severely diabetic rabbit after 30 days treatment.

In the kidneys of the untreated severely diabetic rabbits proliferation of the small blood vessel walls, focal areas of inflammation with mononuclear cell infiltrates and fibrosed glomeruli were observed. In several animals, hyalinized material was present in the glomeruli and there were areas of calcification in and around the glomeruli and renal tubules (FIGS. 9 and 10). In the treated group of severely diabetic rabbits, with the exception of pyelonephritic changes, other pathological alterations were no longer observed (FIG. 11). Thus, Menthi administration arrests the progression of the nephropathy with likely improvement in kidney function.

Figure 12:
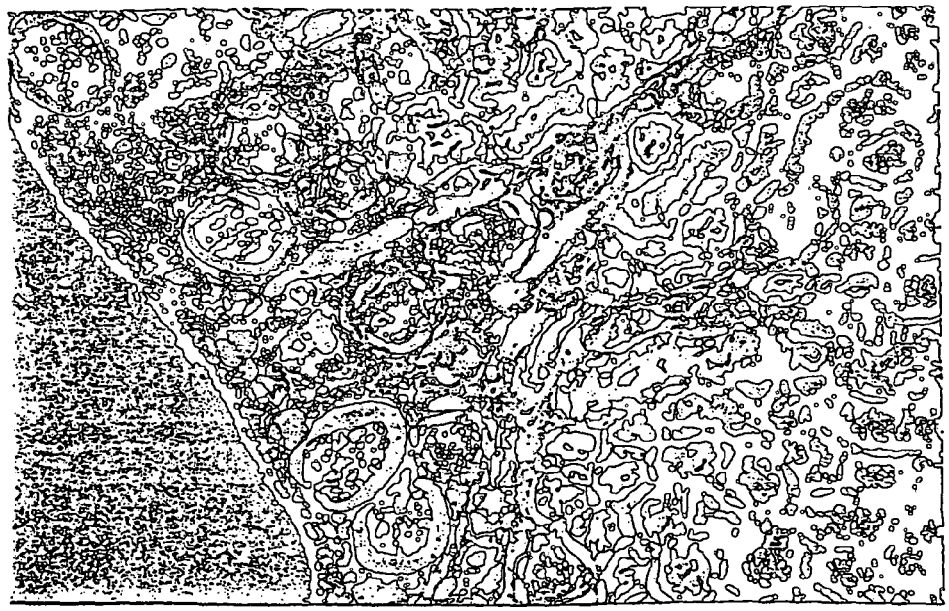
FIG. 12 is a photomicrograph of renal tissue of an untreated diabetic rabbit showing subcapsular scarring.
Figure 13:
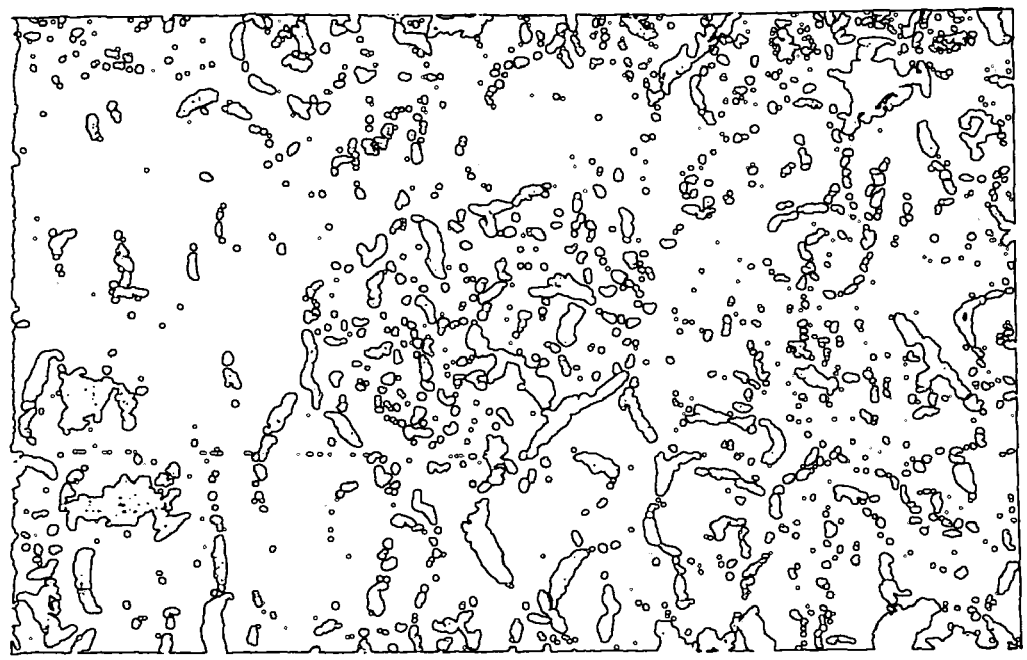
FIG. 13 is a photomicrograph of normal kidney of a diabetic rabbit after 30 days treatment.
Figure 14:
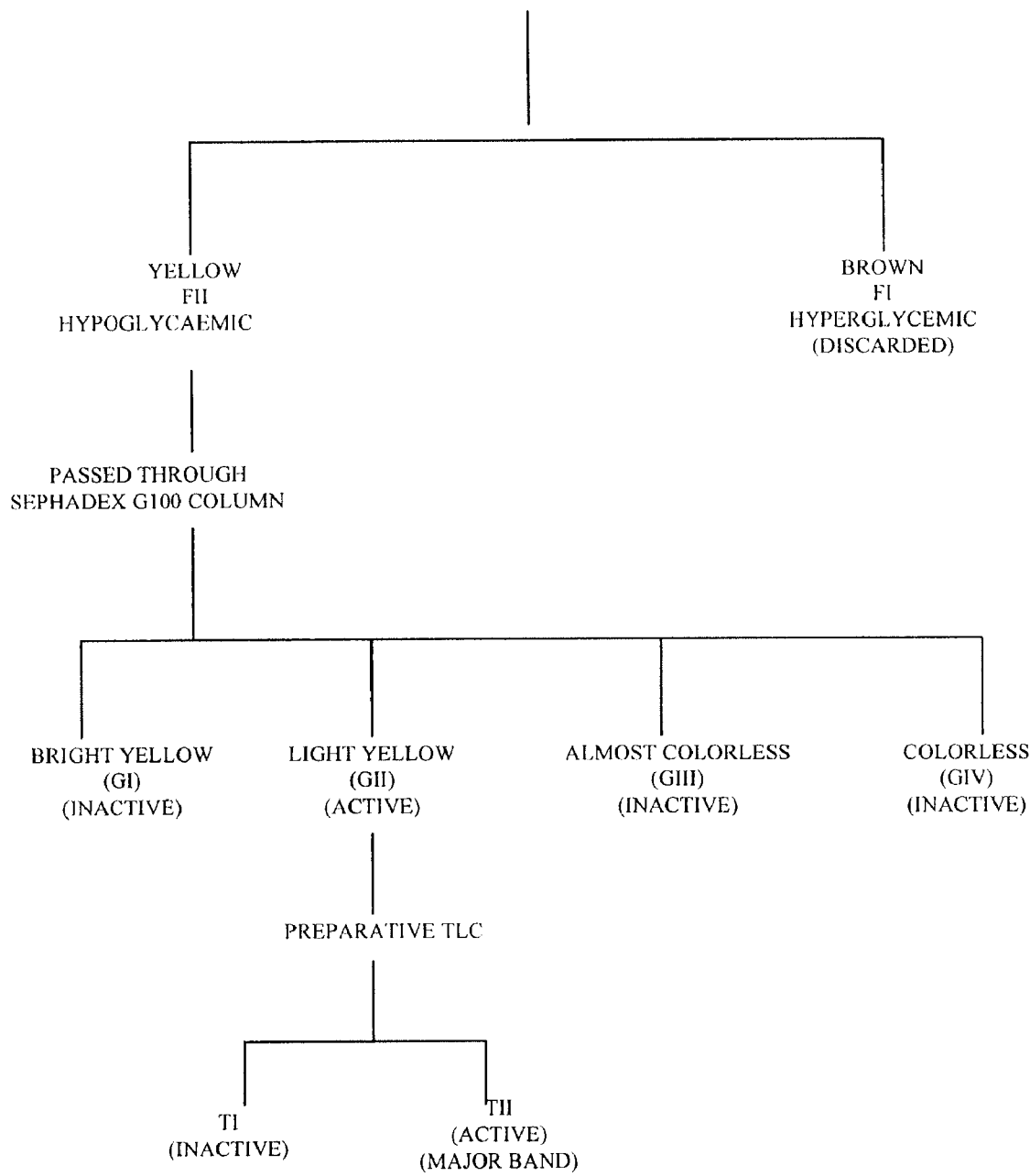
FIG. 14 is a flow chart of the isolation procedure of water extract of the fenugreek seeds passed through DEAE-cellulose column.

In the untreated subdiabetic and diabetic group, no renal pathology was observed except for one diabetic rabbit, in which subcapsular scarring was observed (FIG. 12). In the treated group of subdiabetic and diabetic rabbits, no abnormal histological changes were observed (FIG. 13).

The above studies demonstrate that Menthi treatment either halted the progression or reversed the histopathological abnormalities observed in untreated diabetic rabbits. Furthermore, these studies demonstrate that Menthi treatment does not produce abnormal histopathological changes.

Example X

This example describes the hypocholesterolemic activity of an invention composition.

Induction of Hypercholesterolemia:

Cholesterol was suspended in groundnut oil by a vortex mixer. Each rabbit was given a single dose of 100 mg/kg/day of cholesterol orally as indicated below.

Hypocholesterolemic Effect of Menthi GII:

Animals fed cholesterol (100 mg/kg/day) via gastric intubation with Ryle's tube for one week were randomized into two groups. Group I and II animals each continued to receive cholesterol 100 mg/kg/day, while group II animals also received Menthi GII (in addition to cholesterol) at a dose of 50 mg/kg/day for five weeks. This method differs from the conventional method, which is to feed rabbits cholesterol until hypercholesterolemia is induced, withdraw cholesterol to both control and experimental groups, and give the drug to the experimental group. The conventional method suffers from the disadvantage that blood cholesterol level naturally decreases in the untreated control group following cholesterol withdrawal. The effect of a drug with only a slight cholesterol-lowering effect would therefore be masked due to the naturally occurring decrease in the control group. The method used herein detects compounds with even a slight cholesterol-lowering effect.

Serum total cholesterol (TC), HDL cholesterol (HDLC), LDL cholesterol (LDLC) plus VLDL cholesterol (VLDLC) and triglycerides were determined every week, using kits from Ranbaxy Diagnostics, New Delhi (Table 16). Serum cholesterol levels gradually increased in both groups of animals and reached significantly higher levels at the end of the first week. In the untreated group, levels increased from 54±7.0 to 123±11.8 mg/dl and 59±15 to 114±11.6 mg/dl in the group designated for treatment. Similarly, the level of LDL+VLDL cholesterol and triglycerides increased significantly in both the groups (Table 17). Thus, the degree of hypercholesterolemia was the same in both groups before commencement of treatment.

In the control group, total cholesterol continued to increase and reached, at the end of the fifth week, 285±17 mg/dl (a 428% increase). In contrast, in the fenugreek treated test group, cholesterol decreased to 97±11 mg/dl, i.e., a 15% decrease from day 7 value (Table 16). When compared with the day 1 normal values, cholesterol increased only 64% compared with a 428% increase in untreated controls. Likewise, in the control group, there was a marked increase of LDL+VLDL from 97±10 mg/dl on day 7 to 257±14 mg/dl by the end of fifth week, whereas, in the treated group a marginal rise in cholesterol, from 88±10 mg/dl at the end of first week to 96±22 mg/dl by the end of fifth week occurred (Table 17). Thus, the fenugreek composition not only countered the elevating effect of cholesterol feeding on total cholesterol and VLDL+LDL cholesterol but also improved the final values. Even the ratios of total cholesterol/HDLC and (VLDL+LDL) C/HDLC decreased following treatment (Table 18). There was no significant change in HDLC levels in either of the two groups, consistent with earlier observations that cholesterol feeding does not significantly effect HDLC levels.

Serum triglyceride levels increased by the end of the first week in both groups. In the following four weeks, the increase was only marginal in the treated group in comparison to the untreated control group, where the triglycerides levels continued to rise to substantially higher levels (Table 19). This shows that the fenugreek composition prevents increase in serum triglycerides. In both groups, no change was observed in the fasting blood glucose levels. This result implies that the hypoglycemic activity of Menthi GII is limited to hyperglycemic states and not in euglycaemic states. This characteristic eliminates the risk of hypoglycemia induced by fenugreek composition, which is an advantage over other drugs.

TABLE 16

EFFECT OF MENTHI ON SERUM TOTAL CHOLESTEROL IN HYPERCHOLESTEROLEMIC RABBITS

Serum Cholesterol (mg/dl)

| Days | Untreated | Treated |
|---|---|---|
| 1 | 54 ± 7 | 59 ± 15 |
| 7 | 123 ± 12 | 114 ± 12 |
| 14 | 156 ± 12 | 118 ± 12 |
| 21 | 230 ± 14 | 116 ± 15 |
| 28 | 281 ± 16 | 100 ± 12 |
| 35 | 285 ± 7 | 97 ± 11 |

N = 5 in each group. The values represent mean ± standard deviation.

TABLE 17

EFFECT OF MENTHI ON SERUM LDL + VLDL CHOLESTEROL LEVELS IN HYPERCHOLESTEROLEMIC RABBITS

Serum LDL + VLDL Cholesterol (mg/dl)

| Days | Untreated | Treated |
|---|---|---|
| 1 | 28 ± 6.8 | 35 ± 14 |
| 7 | 97 ± 10 | 88 ± 10 |
| 14 | 130 ± 10 | 90 ± 10 |
| 21 | 201 ± 12 | 95 ± 13 |
| 28 | 254 ± 16 | 92 ± 19 |
| 35 | 257 ± 14 | 96 ± 22 |

N = 5 in each group. The values represent mean ± standard deviation.

TABLE 18

EFFECT OF MENTHI FROM FENUGREEK SEEDS ON SOME PARAMETERS OF SERUM LIPID PROFILE IN CONTROL AND TREATED RABBITS

| | DAYS | | | | | | % Change (Compared With Day 7 Value) |
|---|---|---|---|---|---|---|---|
| | Day 1 | Day 7 | Day 14 | Day 21 | Day 28 | Day 35 | |
| TEST GROUP: | | | | | | | |
| HDLC (mg %) | 24 ± 5.2 | 24 ± 6.4 | 24 ± 6.1 | 24 ± 5.1 | 25 ± 5.1 | 25 ± 4.8 | +4.1 |
| TC/HDLC | 2.5 | 4.6 | 4.8 | 4.8 | 4.0 | 3.8 | −17% |
| (LDL + VLDL)C/HDLC | 1.4 | 3.8 | 3.9 | 3.9 | 3.0 | 2.9 | −23.7% |
| CONTROL GROUP | | | | | | | |
| HDLC (mg %) | 26 ± 2.3 | 26 ± 2.6 | 26 ± 2.4 | 28 ± 2.1 | 27 ± 2.9 | 28 ± 3.1 | +7.7 |
| TC/HDLC | 2.1 | 4.7 | 6.0 | 7.9 | 10.4 | 10.2 | +117% |
| (LDL + VLDL)C/HDLC | 1.07 | 3.7 | 5.0 | 7.2 | 9.2 | 9.2 | +117% |

N = 5 in each group: The values represent mean ± Standard deviation.

TABLE 19

EFFECT OF MENTHI ON SERUM TRIGLYCERIDES IN HYPERCHOLESTEROLEMIC RABBITS

Serum Triglycerides (mg/dl)

| Days | Untreated | Treated |
|---|---|---|
| 1 | 71 ± 16 | 70 ± 12 |
| 7 | 80 ± 18 | 88 ± 10 |
| 14 | 112 ± 16 | 90 ± 10 |
| 21 | 101 ± 17 | 95 ± 13 |
| 28 | 116 ± 22 | 92 ± 19 |
| 35 | 120 ± 21 | 96 ± 22 |

N = 5 in each group. The values represent mean ± standard deviation.

These results demonstrate that serum cholesterol and triglycerides, even at significantly high levels, can be reduced by administration of fenugreek seed composition. These results also indicate that administration of fenugreek seed composition produces a considerable improvement in all the lipid parameters.

In sum, these results demonstrate that the fenugreek composition, which showed broad spectrum hypoglycemic activity, also has broad spectrum hypolipidemic activity. The insulinotropic activity of the fenugreek composition may mediate the hypoglycemic activity, as suggested by the favorable effects on the lipid profile of insulin treatment. Because hyperglycemia and hypercholesterolemia often develop together, the fenugreek composition, which exhibits both hypoglycemic and hypocholesterolemic activity, has definite advantages.

A number of embodiments of the invention have been described. Nevertheless, it will be understood that various modifications may be made without departing from the spirit and scope of the invention. Accordingly, other embodiments are within the scope of the following claims.

What is claimed is:

1. A composition having blood glucose-lowering or cholesterol-lowering activity produced by
   a. contacting Fenugreek seed or seed part with an aqueous solution, for at least about 2 hours, the solution having less than about 50% ethanol, thereby producing an aqueous extract; and
   b. fractionating by weak anion exchange chromatography the aqueous extract to enrich for a component(s) with a molecular weight less than 500 Daltons and having blood glucose-lowering or cholesterol-lowering activity and to remove a blood glucose-increasing activity, thereby obtaining a composition having blood glucose-lowering or cholesterol-lowering activity without substantial blood glucose-increasing activity.

2. A composition having blood glucose-lowering or cholesterol-lowering activity produced by
   a. contacting Fenugreek seed or seed part with an aqueous solution, for at least about 2 hours, the solution having less than about 50% ethanol; and
   b. fractionating by anion exchange chromatography the aqueous extract to enrich for a component(s) with a molecular weight less than 500 Daltons and having blood glucose-lowering or cholesterol-lowering activity and to remove a blood glucose-increasing activity, thereby obtaining a composition having blood glucose-lowering or cholesterol-lowering activity without substantial blood glucose-increasing activity.

3. The composition of claim 2, wherein the anion exchange chromatography comprises DEAE-cellulose chromatography.

4. The composition of claim 1, further comprising fractionating the composition of step b. by gel filtration.

5. The composition of claim 2, further comprising fractionating the composition of step b. by gel filtration.

6. The composition of claim 1, wherein the aqueous solution comprises water.

7. The composition of claim 2, wherein the aqueous solution comprises water.

8. The composition of claim 2, wherein the contacting of step a is at a temperature between about 4 and 25° C.

9. The composition of claim 2, wherein the contacting of step a is at a temperature between about 4 and 25° C.

* * * * *